United States Patent
Kalafut et al.

(10) Patent No.: US 10,078,725 B2
(45) Date of Patent: Sep. 18, 2018

(54) METHODS AND TECHNIQUES FOR COLLECTING, REPORTING AND MANAGING IONIZING RADIATION DOSE

(71) Applicant: Bayer Medical Care, Inc., Indianola, PA (US)

(72) Inventors: John F. Kalafut, Pittsburgh, PA (US); David A. Mishler, Slippery Rock, PA (US); Sridhar R. Balasubramanian, Monroeville, PA (US); John A. Brosovich, Pittsburgh, PA (US); Frederick P. Windham, Birmingham, AL (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 393 days.

(21) Appl. No.: 14/357,224

(22) PCT Filed: Nov. 19, 2012

(86) PCT No.: PCT/US2012/065918
§ 371 (c)(1),
(2) Date: May 9, 2014

(87) PCT Pub. No.: WO2013/075127
PCT Pub. Date: May 23, 2013

(65) Prior Publication Data
US 2015/0100572 A1  Apr. 9, 2015

Related U.S. Application Data

(60) Provisional application No. 61/560,984, filed on Nov. 17, 2011.

(51) Int. Cl.
*G06F 7/00* (2006.01)
*G06F 17/30* (2006.01)
(Continued)

(52) U.S. Cl.
CPC ...... *G06F 19/321* (2013.01); *G06F 17/30256* (2013.01); *G06K 9/00456* (2013.01);
(Continued)

(58) Field of Classification Search
CPC .................. G06F 19/321; G06F 17/30256
(Continued)

(56) References Cited

U.S. PATENT DOCUMENTS

| 5,713,856 A | 2/1998 | Eggers et al. |
| 6,162,198 A | 12/2000 | Coffey et al. |

(Continued)

FOREIGN PATENT DOCUMENTS

| JP | 2002177238 A | 6/2002 |
| JP | 2003052660 A | 2/2003 |

(Continued)

OTHER PUBLICATIONS

International Search Report and Written Opinion dated Jun. 17, 2014 of corresponding PCT Application No. PCT/US2014/017931.
(Continued)

*Primary Examiner* — Usmaan Saeed
*Assistant Examiner* — Brian E. Weinrich
(74) *Attorney, Agent, or Firm* — James R. Stevenson; Bryan P. Clark

(57) ABSTRACT

Provided is a method of collecting and managing information relating to medical diagnostic procedures which includes collecting objective information about a plurality of procedures and subjective information about the results of those procedures. The objective information provides information about the parameters of the procedure and the patient who underwent the procedure while the subjective information includes an assessment of the quality of the results of the procedure. This information can be stored in a database. The database can be accessed and the information therein (Continued)

used in connection with understanding the results of past procedures and planning for future procedures.

18 Claims, 23 Drawing Sheets

(51) Int. Cl.

| | | |
|---|---|---|
| *G06F 19/00* | (2018.01) | |
| *G06Q 50/24* | (2012.01) | |
| *G06Q 10/10* | (2012.01) | |
| *G06K 9/00* | (2006.01) | |
| *G16H 40/20* | (2018.01) | |
| *G06F 15/16* | (2006.01) | |

(52) U.S. Cl.
CPC ............ *G06Q 10/10* (2013.01); *G06Q 50/24* (2013.01); *G16H 40/20* (2018.01); *G06K 2009/00489* (2013.01)

(58) Field of Classification Search
USPC ........................................................ 707/736
See application file for complete search history.

(56) References Cited

U.S. PATENT DOCUMENTS

| | | | |
|---|---|---|---|
| 6,292,771 B1* | 9/2001 | Haug ................. | G06F 17/2785 704/9 |
| 6,602,488 B1 | 8/2003 | Daghighian | |
| 7,457,804 B2 | 11/2008 | Uber, III et al. | |
| 7,933,782 B2 | 4/2011 | Reiner | |
| 7,996,381 B2* | 8/2011 | Uber, III ............... | G06F 19/324 707/708 |
| 8,147,464 B2 | 4/2012 | Spohn | |
| 8,198,599 B2 | 6/2012 | Bouton | |
| 8,337,456 B2 | 12/2012 | Schriver | |
| 8,521,716 B2 | 8/2013 | UberIII | |
| 2002/0165193 A1 | 11/2002 | Greene | |
| 2003/0023155 A1 | 1/2003 | Tsunoda | |
| 2004/0082918 A1 | 4/2004 | Evans | |
| 2004/0185049 A1 | 9/2004 | Hunter | |
| 2004/0193453 A1 | 9/2004 | Butterfield et al. | |
| 2004/0205343 A1 | 10/2004 | Forth | |
| 2005/0129170 A1 | 6/2005 | Watson | |
| 2007/0019849 A1* | 1/2007 | Kaufman ............. | G06F 19/321 382/128 |
| 2007/0238948 A1* | 10/2007 | Bartsch ................. | G06T 7/0012 600/407 |
| 2007/0282965 A1 | 12/2007 | Kataoka | |
| 2008/0010384 A1 | 1/2008 | Rechterman | |
| 2008/0071210 A1 | 3/2008 | Moubayed et al. | |
| 2008/0086087 A1 | 4/2008 | Spohn | |
| 2008/0109250 A1* | 5/2008 | Walker ................ | G06F 17/2247 705/2 |
| 2008/0131362 A1 | 6/2008 | Rousso | |
| 2008/0200870 A1 | 8/2008 | Palmroos et al. | |
| 2008/0212877 A1* | 9/2008 | Franco ................. | G06K 9/033 382/182 |
| 2008/0294096 A1 | 11/2008 | Uber, III | |
| 2009/0022377 A1* | 1/2009 | Matsue ................. | G06F 19/321 382/128 |
| 2009/0257949 A1 | 10/2009 | Hefti | |
| 2009/0285469 A1 | 11/2009 | Callahan | |
| 2010/0112011 A1 | 5/2010 | Friedberg | |
| 2010/0183206 A1* | 7/2010 | Carlsen ................. | A61B 6/032 382/128 |
| 2010/0183208 A1* | 7/2010 | Kondo ................. | G06F 19/321 382/128 |
| 2010/0185040 A1 | 7/2010 | Uber | |
| 2010/0256459 A1* | 10/2010 | Miyasa ................. | G06Q 50/22 600/300 |
| 2011/0076317 A1 | 3/2011 | Alessi | |
| 2011/0093504 A1 | 4/2011 | Butler | |
| 2011/0178359 A1 | 7/2011 | Hirschman | |
| 2011/0191822 A1 | 8/2011 | Pinsky | |
| 2011/0209764 A1 | 9/2011 | Uber | |
| 2012/0123257 A1 | 5/2012 | Stokes | |
| 2012/0219615 A1 | 8/2012 | Hershberg | |
| 2012/0283691 A1 | 11/2012 | Barnes et al. | |
| 2013/0024208 A1* | 1/2013 | Vining ................. | A61B 6/467 705/3 |
| 2013/0123567 A1 | 5/2013 | Agamaite | |
| 2013/0259891 A1 | 10/2013 | Harn | |
| 2014/0039446 A1 | 2/2014 | Day et al. | |
| 2014/0046295 A1 | 2/2014 | Uber | |

FOREIGN PATENT DOCUMENTS

| | | |
|---|---|---|
| WO | 1999045783 | 9/1999 |
| WO | 2001023004 | 4/2001 |
| WO | 2008083313 | 7/2008 |
| WO | 2009042577 | 4/2009 |
| WO | 2012155035 | 5/2011 |
| WO | 2011137374 | 11/2011 |

OTHER PUBLICATIONS

International Search Report and Written Opinion from PCT Application No. PCT/US2012/066792, filed Nov. 28, 2012.
CT Scan Protocols. Dr. Elliot K. Fishman. www.CTisus.com, Feb. 14, 2014.
Medrad Stellant with Certegra Workstation Operation Manual, Catalog #SCT 310, 3033828 Rev. C, 2012, Indianola, PA, USA.
Sibun.: 'Language Determination: Natural Language Processing from Scanned Document Images.', [Online] 1994, XP003031315 Retrieved from the Internet: &It;URL:http://citeseerx.ist.psu.edu/viewdoc/summary?doi=10.1.1.14.8980> [retrieved on Jan. 18, 2013].
Supplementary Search Report from corresponding EP Application No. 12849991.0.
International Preliminary Report on Patentability dated May 30, 2014 from corresponding PCT Application No. PCT/US2012/065918.
Anonymous., "Natural language processing—Wikipedia, the free encyclopedia retrieved from internet: URL: http://en.wikipedia.org/w/index.php?title=Natural_language_processing&oldid=460032699 [retrieved on Apr. 28, 2015,]", Nov. 10, 2011.

\* cited by examiner

PATIENT NAME: MEDRAD T31
ACCESSION NUMBER: 20110919144130
PATIENT ID: M3
EXAM DESCRIPTION: PERFUSION

EXAM No: 9277
SEP 20 2011
LightSpeed VCT

DOSE REPORT

| SERIES | TYPE | SCAN RANGE (mm) | CTDIvol (mGy) | DLP (mGy-cm) | PHANTOM (cm) |
|---|---|---|---|---|---|
| 1 | SCOUT | | | | |
| 2 | CINE | $0.000-$35.000 | 407.60 | 1630.41 | HEAD 16 |
| | | TOTAL EXAM DLP: | | 1630.41 | |

Certegra™ Informatics Platform

CERTEGRA DASHBOARD

| CERTEGRA DASHBOARD | BHM MAIN CT4 | CT1 | CT2 | TOTALS | COST |
|---|---|---|---|---|---|
| TOTAL CONTRAST DELIVERED | 166,434.49 ml | 299,009.56 ml | 195,837.09 ml | 661,281.14 ml | $66,128.11 |
| TOTAL SALINE DELIVERED | 140,884.67 ml | 194,021.37 ml | 120,549.21 ml | 455,455.25 ml | $91.09 |
| CONTRAST WASTE | 12,862.61 ml | 23,615.04 ml | 9,442.84 ml | 45,920.49 ml | $4,592.05 |
| SALINE WASTE | 19,695.26 ml | 40,910.94 ml | 22,472.97 ml | 83,079.17 ml | $16.62 |
| AVERAGE PEAK CONTRAST FLOW RATE | 4.09 ml/s | 3.07 ml/s | 2.95 ml/s | 3.37 ml/s | |
| AVERAGE PEAK SALINE FLOW RATE | 4.33 ml/s | 2.91 ml/s | 2.80 ml/s | 3.34 ml/s | |
| AVERAGE PEAK PRESSURE CONTRAST | 164 psi | 141 psi | 119 psi | 141 psi | |
| AVERAGE PEAK PRESSURE SALINE | 147 psi | 141 psi | 100 psi | 120 psi | |
| SINGLE SYRINGE KITS | 26 KITS | 129 KITS | 71 KITS | 226 KITS | $1,808.00 |
| DUAL SYRINGE KITS | 1676 KITS | 3458 KITS | 2362 KITS | 7496 KITS | $112,440.00 |
| SAMPLE START DATE | 1/24/2011 | 1/25/2011 | 2/23/2011 | TOTAL COST TO DELIVER CONTRAST | $185,075.87 |
| SAMPLE END DATE | 7/28/2011 | 7/18/2011 | 7/28/2011 | COST OF WASTE (SALINE & CONTRAST) | $4,608.66 |

| CONTRAST BREAKDOWN | BHM MAIN CT4 | CT1 | CT2 | TOTALS | CONTRAST COST |
|---|---|---|---|---|---|
| 240mg/ml LOADED | 0.00 ml | 0.00 ml | 0.00 ml | 0.00 ml | $0.00 |
| 240mg/ml INJECTED | 0.00 ml | 0.00 ml | 0.00 ml | 0.00 ml | $0.00 |
| 240mg/ml WASTE | 0.00 ml | 0.00 ml | 0.00 ml | 0.00 ml | $0.00 |

FIG.13A

COMPARE MULTIPLE INJECTION PROTOCOLS SIDE BY SIDE

Protocol Name: ABD PEL

Values

| Injection | Average Delivered | Average Wasted | Average Flow |
|---|---|---|---|
| 377 | 72.90 ml | 3.27 ml | 3.17 ml/s |

Protocol Name: ABD-PELV W PATENCY

Values

| Injection | Average Delivered | Average Wasted | Average Flow |
|---|---|---|---|
| 4 | 55.92 ml | 0.45 ml | 2.37 ml/s |

Protocol Name: ABD PEL*

Values

| Injection | Average Delivered | Average Wasted | Average Flow |
|---|---|---|---|
| 1502 | 72.50 ml | 3.32 ml | 2.47 ml/s |

Protocol Name: ABD-PELV W PATENCY*

Values

| Injection | Average Delivered | Average Wasted | Average Flow |
|---|---|---|---|
| 7 | 41.30 ml | 4.48 ml | 1.61 ml/s |

FIG. 14

Certegra
Informatics Platform

REPEAT INJECTION ANALYSIS

- REPORT SHOW STUDY ID IN WHICH MORE THAN ONE INJECTIONS OCCURRED

| Key Field | Study ID |
|---|---|
| | ☐ Patient ID |
| | ☐ Accession Number |
| Show Field | ☐ First and Last Name |
| Suite | (All) |

| Study ID | Start | Study Description | Termination | A New Syringe | A loaded (ml) | A Delivered (ml) | A Wasted (ml) | A Peak Pressure (psi) | Count |
|---|---|---|---|---|---|---|---|---|---|
| ⊙ 391 | ⊙ 1/24/2011 19:01 | ⊙ CHEST CT PE PROTOCOL W | ⊙ Disarm | Y | 104.5 | 19.71 | 0 | 278 | 1 |
| | ⊙ 1/24/2011 19:29 | ⊙ CHEST CT PE PROTOCOL W | ⊙ Disarm | N | 88.26 | 62.05 | 26.22 | 141 | 1 |
| 391 Total | | | | | 192.76 | 81.76 | 26.22 | 209.5 | 2 |
| ⊙ 411 | ⊙ 1/25/2011 22:07 | ⊙ BRAIN CT WO CON | ⊙ Completed OK | Y | 124.56 | 14.7 | 0 | 92 | 1 |
| | ⊙ 1/25/2011 22:09 | ⊙ BRAIN CT WO CON | ⊙ Completed OK | N | 109.58 | 108.75 | 0.83 | 151 | 1 |
| 411 Total | | | | | 234.14 | 123.45 | 0.83 | 121.5 | 2 |

FIG.15

Certegra
Informatics Platform — COMPARE INJECTION PROTOCOLS TO PROTOCOLS USED ON THE SCANNER THE PIVOT BELOW ALLOWS FOR SELECTION OF THE INJECTION PROTOCOL(INJECTOR) AND THE DISPLAY OF ALL THE ASSOCIATED STUDY DESCRIIPTIONS(SCANNER). IT SHOWS THE FREQUENCY THAT EACH SCANNER PROTOCOL ALONG WITH CONTRAST BREAK DOWNS FOR EACH PROTOCOL. YOU CAN ALSO FILTER BY CT SUITE Injector Protocol
Protocol Name — (Multiple Items)
Suite — (All)

| Study Description | Values Injection | Utilization | Avg Flow Rate | Avg Delivered | Avg Wasted |
|---|---|---|---|---|---|
| SINUS FACIAL MAXIL CT | 16 | 0.85% | 2.05 ml/s | 69.14 ml | 4.33 ml |
| CHEST CT PE PROTOCOL W | 68 | 3.62% | 3.89 ml/s | 82.55 ml | 7.89 ml |
| ABD PEL CT W IV W PO C | 670 | 35.66% | 2.56 ml/s | 72.94 ml | 3.04 ml |
| ABD PEC CT W IV WO PO | 858 | 45.66% | 2.60 ml/s | 72.01 ml | 2.77 ml |
| NECK CT W CON | 49 | 2.61% | 2.28 ml/s | 68.14 ml | 4.99 ml |
| ABD PEL CT W IV WO PO CON | 1 | 0.05% | 3.14 ml/s | 74.75 ml | 23.96 ml |
| CHEST CT W CON | 62 | 3.30% | 2.64 ml/s | 75.66 ml | 3.11 ml |
| ABD CT W IV WO PO CON | 20 | 1.06% | 2.52 ml/s | 66.02 ml | 7.17 ml |
| ... | 55 | 2.93% | 2.72 ml/s | 69.77 ml | 5.36 ml |
| BRAIN CT WO CON | 3 | 0.16% | 2.10 ml/s | 73.06 ml | 0.91 ml |

THE PIVOT BELOW ALLOWS FOR SELECTION OF THE SCANNER PROTOCOL AND THE DISPLAY OF ALL THE ASSOCIATED PROTOCOLS THAT WERE USED ON THE INJECTOR. IT SHOWS THE FREQUENCY THAT EACH SCANNER PROTOCOL ALONG WITH CONTRAST BREAKDOWNS FOR EACH PROTOCOL. YOU CAN ALSO FILTER BY CT SUITE

Scanner Study
Study Description — ABD PEL CT W IV W POC
Suite — (All)

| Protocol Name | Values Injection | Utilization | Avg Flow Rate | Avg Delivered | Avg Wasted |
|---|---|---|---|---|---|
| Protocol | 2 | 0.11% | 2.42 ml/s | 71.07 ml | 0.70 ml |
| ABD PEL* | 525 | 28.94% | 2.39 ml/s | 73.06 ml | 3.02 ml |
| ABD PEL | 145 | 7.99% | 3.17 ml/s | 72.52 ml | 3.12 ml |
| PE* | 7 | 0.39% | 2.63 ml/s | 65.46 ml | 3.03 ml |
| ... | 1 | 0.06% | 0.00 ml/s | 0.00 ml | 0.00 ml |
| ABD - PELV W PATENCY* | 2 | 0.11% | 1.59 ml/s | 37.48 ml | 0.30 ml |
| P3T Abdomen | 5 | 0.28% | 2.71 ml/s | 102.41 ml | 0.75 ml |
| NECK* | 3 | 0.17% | 1.87 ml/s | 73.78 ml | 1.86 ml |
| CHEST OR ABD PELVIS* | 711 | 39.20% | 2.11 ml/s | 68.69 ml | 5.10 ml |
| BRAIN C | 1 | 0.06% | 2.11 ml/s | 73.43 ml | 1.09 ml |

METHODS AND TECHNIQUES FOR COLLECTING, REPORTING AND MANAGING IONIZING RADIATION DOSE

CROSS REFERENCE TO RELATED APPLICATIONS

This application is a 371 national phase application of PCT International Application No. PCT/US2012/065918, filed Nov. 19, 2012, and designating the United States of America, which claims benefit of U.S. Provisional Patent Application Ser. No. 61/560,984, filed Nov. 17, 2011, the entire contents of which are hereby incorporated by reference.

BACKGROUND OF THE INVENTION

Field of the Invention

This disclosure relates to methods and techniques for collecting, reporting, and managing information about medical diagnostic procedures, as well as analyzing and using such information. Also provided are systems which implement the methods and techniques described herein.

Description of Related Art

The following information is provided to assist the reader to understand the environment in which the methods and techniques for collecting, reporting, and managing information about medical diagnostic procedures of this disclosure will typically be used. Specific terms used herein are not intended to be limited to any particular narrow interpretation unless clearly stated otherwise in this document. References set forth herein may facilitate understanding of the methods and techniques for collecting, reporting, and managing information about medical diagnostic procedures of this disclosure. The disclosure of all references cited herein is incorporated by reference.

In order to assess the efficacy of a change in a medical technique, technology, or standard, a physician must perform the procedure, use the technology, or test the new standard with a number of patients in a number of multi-site clinical trials. Naturally, those trials must include a control group for proper assessment of the medical technique, technology, or standard.

Following clinical trials, the physician typically describes and publishes his findings in a suitable medical journal. In addition, he may present his findings to his peers at medical conferences. As can be readily understood, this process often may take a number of years.

Moreover, the sheer magnitude of the undertaking often means that only the most deserving of medical techniques and technologies and the establishment of the most beneficial standards are pursued.

In addition, the enormous costs associated with studies prohibit most doctors and physicians from testing any techniques or equipment or from establishing new standards without assistance from large companies and research organizations that have sufficient financial resources to fund these activities.

For example, when performing a diagnostic evaluation that involves the use of a medical injector in combination with a scanning device (such as a CT (Computed Tomography) or MRI (Magnetic Resonance Imaging) scanner), it may be the widely accepted practice to inject contrast media into the patient at a rate of X ml per minute to assure that the diagnostic evaluation provides useable information to the physician. The standard rate of injection probably was established through the clinical trial method described above. This standard rate may be expected to provide a certain level of enhancement.

However, it may be that the rate of injection of contrast media may not need to be as high as the rate initially thought because, due to slight variations in scanning technology, patient demographics, or other protocol measures, an optimal result could have been achieved using less contrast media. For example, the sensitivity of the scanner used for a particular diagnostic may have improved (and probably has improved) since the development of the standard(s) associated with its use. By way of another example, the model patient for which the standard was developed may vary slightly in height or weight from the patient now subject to the imaging procedure. Some doctors will adapt their protocols to the capabilities of the new equipment or otherwise adapt to the changed circumstances. However, other practitioners, despite advances in technology, may continue to use the established contrast flow rate simply because the flow rate falls within the standard established for the particular diagnostic technique.

Not only does this increase the cost of the procedure (because more contrast media is used than is required), it also increases the possibility that the patient may have an adverse reaction to the contrast media. In addition, and perhaps more importantly, due to its increased sensitivity, the scanner's performance may be hindered by the use of contrast media at the standard rate if it performs optimally at a lower injection rate that is not recognized by the standard. Similarly, practitioners may be oblivious to improvements realized by other practitioners who have successfully achieved optimal study results using protocols that diverge from what, at one time, was the accepted practice or which are more closely tailored to the actual study being performed.

In summary, what the prior art and current practice fails to provide is a system or methodology for the appropriately rapid adoption of advances in medicine that develop on a continuing basis, the kind of incremental changes that result from daily practice. There are few existing mechanisms by which incremental advances and successful results may be shared with other practitioners in the medical profession to more rapidly advance medical care and quality, among other things.

SUMMARY OF THE INVENTION

In one aspect, a method of collecting and managing information relating to medical imaging procedures is provided. The method can involve collecting information about a plurality of medical imaging procedures from a plurality of information sources. The information collected for each of the medical imaging procedures can include objective information about the medical imaging procedure and a subjective assessment of a result of the medical imaging procedure. The objective information can include at least information about the parameters of the medical imaging procedure and information about the patient that underwent to the medical imaging procedure. The method can further involve forming a plurality of procedure records, wherein each of the procedure records corresponds to one of the medical imaging procedures, and wherein each of the procedure records includes at least the objective information about the medical imaging procedure and the subjective assessment of the result of the medical imaging procedure. In addition, the method can involve storing the procedure records in a database, wherein the database is in electronic communication with at least a portion of the information sources.

In certain non-limiting embodiments, the information sources can include a plurality of medical imaging devices. The information sources can include at least one medical record system comprising a digitized image or document that is associated with one of the medical imaging procedures. In some non-limiting embodiments, the information sources can include a plurality of medical imaging devices and at least one medical record system.

In certain non-limiting embodiments, collecting information from the medical record system can involve extracting information from the image using at least one of optical character recognition and natural language processing. In certain non-limiting embodiments, optical character recognition is performed using an optical character recognition engine which includes a font database, wherein the font database comprises font characteristic information that has been specifically adapted for use with the image. Optical character recognition can include a residual error correction process in which one or more errors that have occurred during the optical character recognition are detected and corrected and information about the errors is transferred to the font database.

In some non-limiting embodiments, natural language processing can be used to identify language within the image that is indicative of a subjective assessment of the result of the medical imaging procedure.

In certain non-limiting embodiments, the method can further involve transferring the information stored in the database to a data reporting and analysis application, wherein the data reporting and analysis application generates one or more reports based on the information stored in the database.

In certain non-limiting embodiments, the subjective assessment of the result of the medical imaging procedure is an individual's opinion that relates to the quality of the result of the medical imaging procedure.

In certain non-limiting embodiments, for at least a portion of the procedure records, the information sources from which the objective information about the medical imaging procedure and the subjective assessment of the result of the medical imaging procedure are collected are different.

In certain non-limiting embodiments, for at least a portion of the procedure records, the information sources from which the objective information about the medical imaging procedure and the subjective assessment of the result of the medical imaging procedure are collected are the same.

In certain non-limiting embodiments, at least one of the information sources is a medical imaging device, wherein the medical imaging device performs a medical imaging procedure and generates an electronic report thereof, and wherein the subjective assessment of the result of the medical imaging procedure is entered into and stored as part of the electronic report. In some embodiments, the subjective assessment can be entered into the electronic report at a user interface associated with the medical imaging device. In some embodiments, the subjective assessment can be entered into the electronic report at a computer workstation. In certain embodiments, the electronic report can be structured to include a set of pre-defined attribute fields and the subjective assessment is entered into one of the pre-defined fields.

In another aspect, provided is a method of determining a protocol for use in a medical imaging procedure to be performed on a subject patient. The method can involve receiving information about the subject patient. The method can further involve accessing a database, the database including a plurality of procedure records, wherein each of the procedure records corresponds to an imaging procedure that was previously performed, and wherein each of the procedure records contains objective information about the imaging procedure and a subjective assessment of a result of the imaging procedure, the objective information including at least information about the patient who underwent the imaging procedure and information on a protocol used for the imaging procedure. The method can further involve determining a suggested protocol, wherein the suggested protocol is determined based on a consideration of the information of the subject patient and the objective information and subjective assessments contained in the database. In addition, the method can involve presenting the suggested protocol in a visually perceptible form.

In certain non-limiting embodiments, the method can involve modifying the suggested protocol.

In another aspect, provided is a method of collecting and utilizing information about a plurality of medical imaging procedures. The method can involve receiving information about a subject patient on which a medical imaging procedure is to be performed. The method can further involve accessing a database, the database including a plurality of procedure records, wherein each of the procedure records corresponds to a past imaging procedure, and wherein each of the procedure records contains objective information about the past imaging procedure and a subjective assessment of a result of the past imaging procedure, the objective information including at least information about the patient who underwent the past imaging procedure and information on a protocol used for the past imaging procedure. The method can further involve determining a suggested protocol, wherein the suggested protocol is determined based on a consideration of the information of the subject patient and the objective information and the subjective assessment contained in the plurality of records. The method can additionally involve presenting the suggested protocol in a visually perceptible form. The method can also involve performing the medical imaging procedure on the subject patient in accordance with one of the suggested protocol and a modification thereof. In addition, the method can involve providing a subjective assessment of a result of the medical imaging procedure performed on the subject patient, collecting objective information about the medical imaging procedure performed on the subject patient and the subjective assessment of the result of the medical imaging procedure performed on the subject patient, forming a subject patient procedure record comprising the objective information about the medical imaging procedure performed on the subject patient and the subjective assessment of the result of the medical imaging procedure performed on the subject patient, and storing the subject patient procedure record in the database.

In one embodiment, the method can further involve receiving information about a second subject patient on which a medical imaging procedure is to be performed, accessing the database, the database further including the subject patient procedure record, and determining a second suggested protocol, wherein the second suggested protocol is determined based on a consideration of the information of the second subject patient and the objective information and the subjective assessment contained in the plurality of procedure records, including the objective information and the subjective assessment contained in the subject patient procedure record.

In yet another aspect, provided is a medical imaging system. The medical imaging system can include a plurality of medical imaging devices, wherein each of the medical imaging devices is configured to perform a medical imaging procedure according to an imaging protocol provided to the medical imaging device. The system can further include one or more protocol management applications, wherein each of the protocol management applications is in electronic communication with one or more of the medical imaging devices and wherein each of the protocol management applications is configured to deliver the imaging protocol to the medical imaging device. In addition, the system can include a database in electronic communication with each of the protocol management applications, wherein the database includes a plurality of procedure records, wherein each of the procedure records comprises objective information about a past medical imaging procedure and a subjective assessment of the result of the past medical imaging procedure. The objective information includes at least information about the parameters that were used in the past medical imaging procedure and information about the patient that was the subject of the past medical imaging procedure. The database is in electronic communication with a plurality of information sources configured to provide to the database objective information about the medical imaging procedures and subjective assessments of the results of the medical imaging procedures.

In certain non-limiting embodiments, the information sources can include at least one medical record system.

In another aspect, a distributed system for determining a protocol for use in a medical imaging procedure to be performed on a subject patient is provided. The distributed system can include a server having access to a database, wherein the database includes a plurality of procedure records, wherein each of the procedure records corresponds to a past imaging procedure, and wherein each of the procedure records contains objective information about the past imaging procedure and a subjective assessment of a result of the past imaging procedure, the objective information including at least information about the patient who underwent the past imaging procedure and information on a protocol used for the past imaging procedure. The system can further include one or more clients, each of the clients being in electronic communication with the server and being configured to execute a protocol management application that is in electronic communication with a medical imaging device. For each of the clients, the protocol management application can be configured to receive from the client information about the subject patient on which the medical imaging procedure is to be performed, determine a suggested protocol based on a consideration of the information of the subject patient received from the client and the objective information and the subjective assessment contained in the plurality of records accessed from the database, and deliver the suggested protocol to the medical imaging device so as to enable the medical imaging procedure to be performed thereby on the subject patient in accordance with one of the suggested protocol and a modification thereof by an operator of the client.

In certain non-limiting embodiments of the system, the protocol management application is further configured to, for each of the clients, enable the operator to make a subjective assessment of a result of the medical imaging procedure that was performed on the subject patient, collect objective information about the medical imaging procedure performed on the subject patient, form a subject patient procedure record including the objective information about the medical imaging procedure performed on the subject patient and the subjective assessment of the result of the medical imaging procedure performed on the subject patient, and store in the database the subject patient procedure record.

The foregoing exemplary embodiments and other embodiments, along with the attributes and attendant advantages thereof, will best be appreciated and understood in view of the following detailed description taken in conjunction with the accompanying drawings.

BRIEF DESCRIPTION OF THE FIGURES

FIG. 6 illustrates a representative example of one aspect of an optical character recognition error correction technique according to the present disclosure.

FIG. 9 illustrates a representative user interface display for entry of subjective assessment information according to the present disclosure.

FIG. 14 illustrates another representative format in which information can be presented using a data analysis and reporting application according to the present disclosure.

FIG. 15 illustrates another representative format in which information can be presented using a data analysis and reporting application according to the present disclosure.

FIG. 16 illustrates another representative format in which information can be presented using a data analysis and reporting application according to the present disclosure.

FIG. 18 illustrates a representative example of a user display and interface for presenting information according to the present disclosure.

DESCRIPTION OF THE PREFERRED EMBODIMENTS

Figure 1:
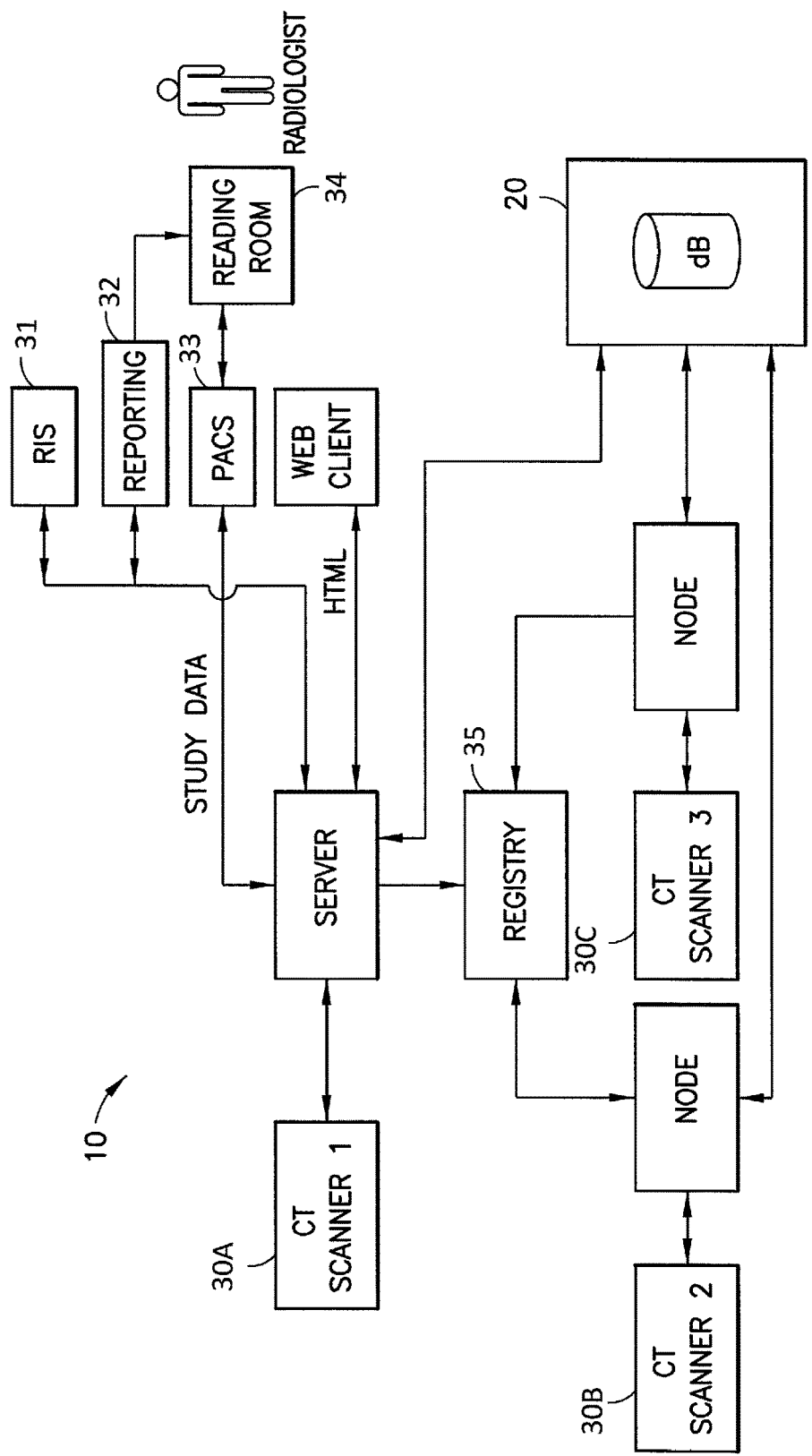
FIG. 1 illustrates a flowchart for a representative embodiment of a system according to this disclosure.
Figure 2:
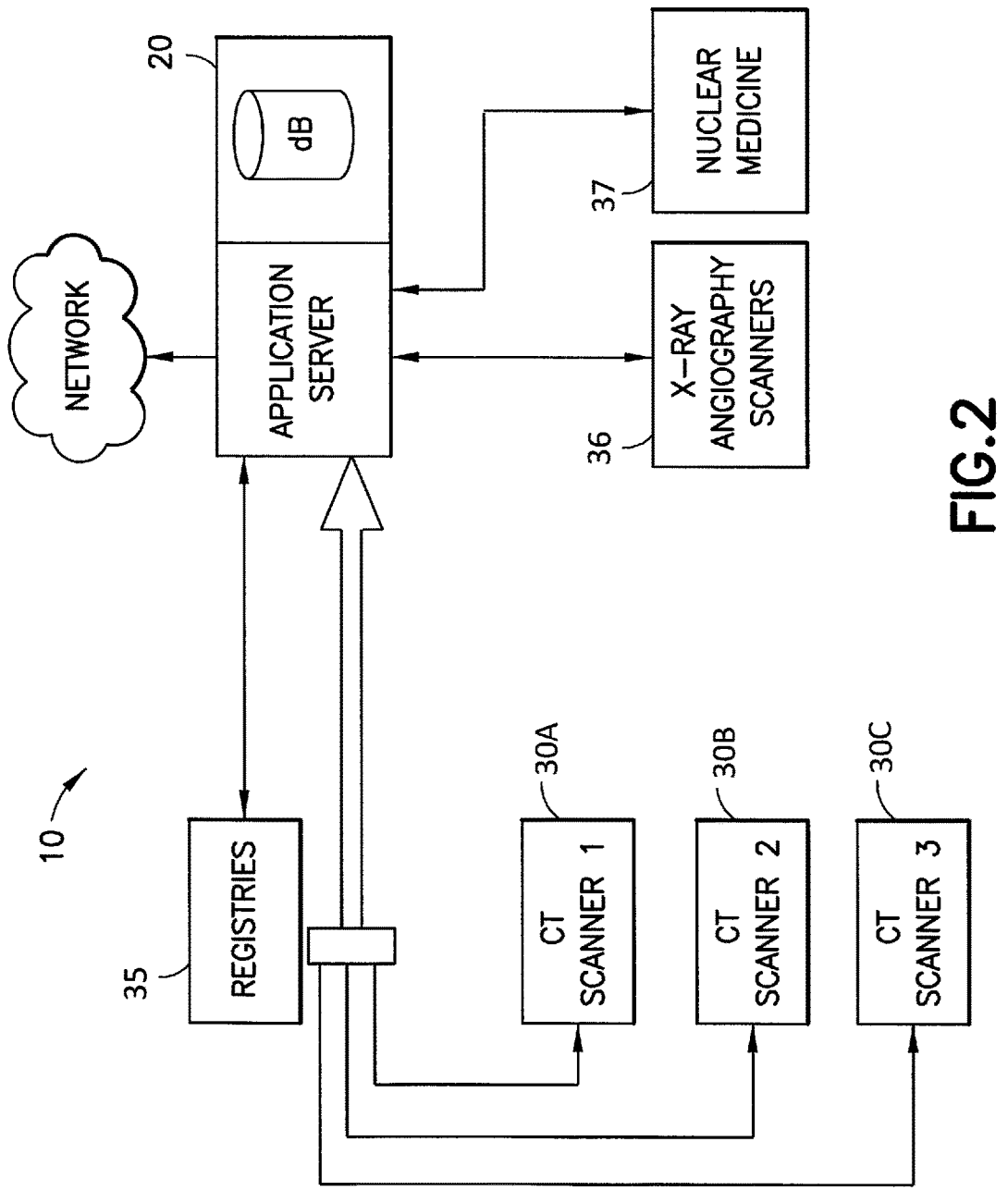
FIG. 2 illustrates a flowchart for a second representative embodiment of a system according to this disclosure.
Figure 3:
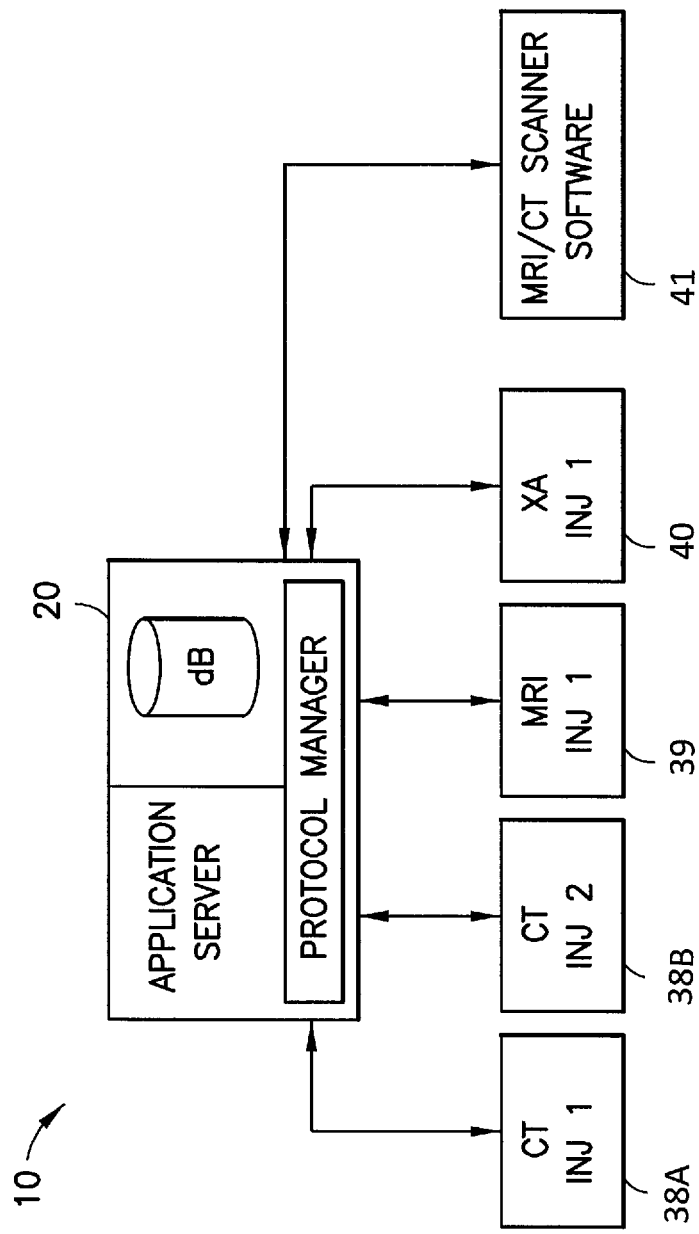
FIG. 3 illustrates a flowchart for a third representative embodiment of a system according to this disclosure.

FIGS. 1-3 illustrate several embodiments of a system 10 according to this disclosure. System 10 can include a database 20 (referred to in the Figures as "dB") for collecting and storing information concerning medical diagnostic procedures from a variety of information sources 30-41. While database 20 is represented as a single unit, database 20 can be comprised of a series of units which are in electronic communication with one another. Database 20 can be populated from a variety of different information sources 30-41, each of which may be in electronic communication with database 20 and/or with each other. As will be described herein, these sources can include medical devices, medical record systems, computer workstations, and other sources of information which are typically involved in gathering, collecting, and/or storing information related to a medical diagnostic procedure, including information about the procedure and information about the patient. These sources 30-41 can provide objective or quantitative information about the patient or procedure itself, such as operating parameters of a medical imaging scanner (e.g., CT SCANNER 1 30A, CT SCANNER 2 30B, CT SCANNER 3 30C, MRI/CT SCANNER SOFTWARE 41, X-RAY ANGIOGRAPHY SCANNERS 36, NUCLEAR MEDICINE 37) and injection systems that deliver contrasting agents into a patient (e.g., CT INJ 1 38A, CT INJ 2 38B, MRI INJ 1 39, and XA INJ 1 40), as well as information about the results of the procedure, which can include some subjective assessment of the quality of the results obtained. Furthermore, estimates of certain information, such as the absorbed, equivalent effective organ and effective radiation dose in an imaging procedure, may be computed based upon procedure information and patient-specific information. A record of each procedure can be created from this information, and the record can be stored in database 20.

Figure 4:
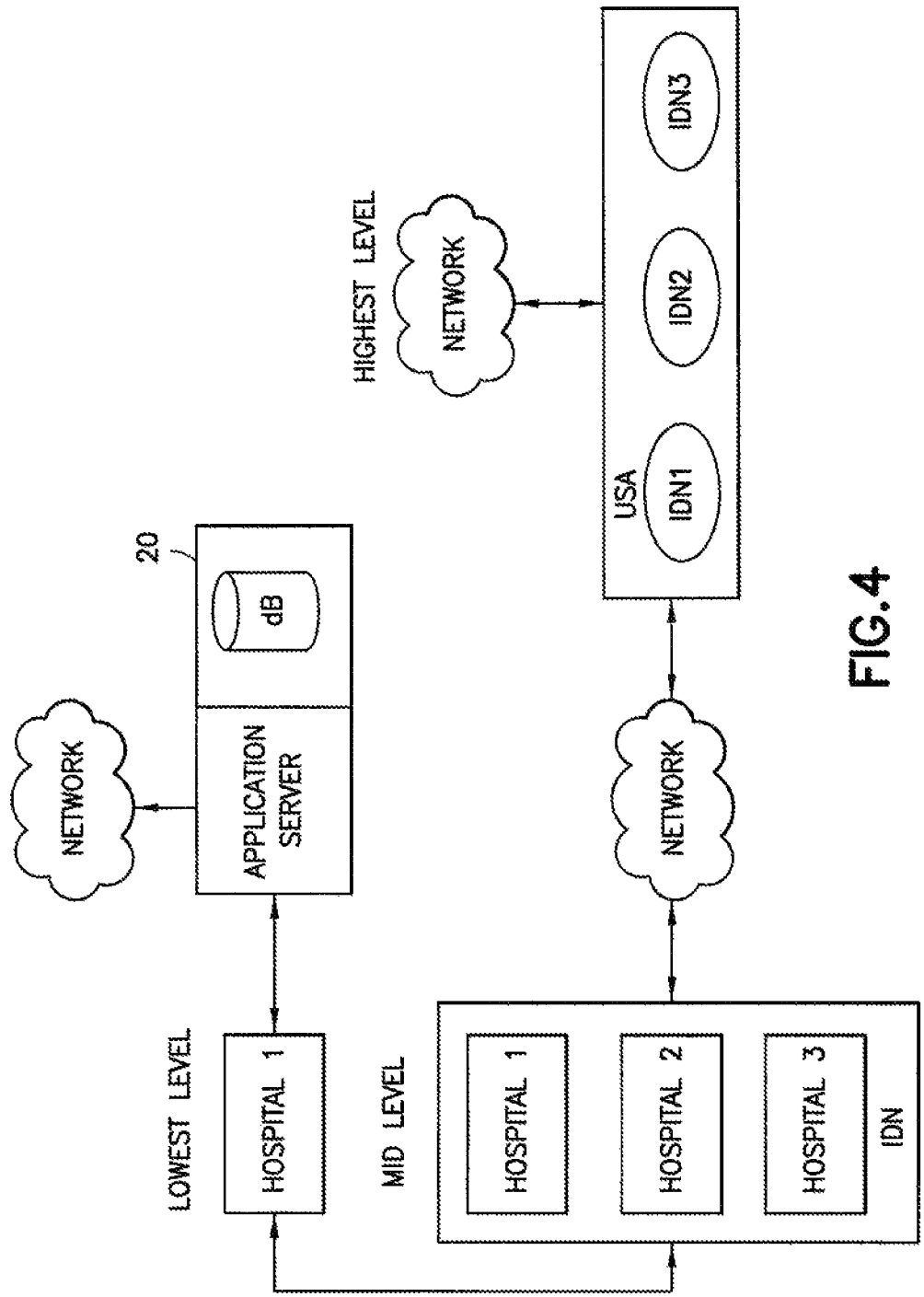
FIG. 4 illustrates a flowchart of one embodiment of a closed loop configuration according to this disclosure.

System 10 can also include one or more components which utilize, either directly or indirectly, information from database 20 in connection with performing one or more medical diagnostic procedures or with analyzing the information stored in database 20. For example, system 10 may be configured such that one or more medical devices can utilize the information stored in database 20 to perform a medical diagnostic procedure. Such medical devices, in some non-limiting embodiments, work in conjunction with one or more protocol management applications which can provide the group of parameters for a procedure to be performed by the medical device. Protocol management applications can be in electronic communication with database 20 and utilize the information therein in determining the appropriate protocol to deliver to the medical device. System 10 may also include one or more data analysis and reporting applications which can analyze information stored in database 20 and generate reports therefrom. Components which utilize information from database 20 may be information sources 30-41 as well. In this sense, system 10 can form a "closed loop" configuration in which previously-collected information is used to developed new information which is then collected and used to generate yet additional information. FIG. 4 illustrates a representative embodiment of certain aspects of a closed loop configuration. For instance, as illustrated in FIG. 4, a radiologist can develop a protocol with the help of a protocoling client in communication with database 20 and protocol management application, the technologist can then deliver the procedure according to the developed protocol, the technologist and/or radiologist can then review the results of the procedure and rate the results, and the results can then be sent to a medical record system and, eventually, provided to database 20.

In some non-limiting embodiments, system 10 can be configured as a distributed system including at least one server and a plurality of clients. For instance, system 10 can be configured to include a server which has access to database 20 and one or more clients capable of communicating with the server. Clients can include components of system that may benefit from access to database 20, including information sources 30-41 as well as medical devices, data reporting and analysis applications, protocol management applications, etc. which may or may not also serve as information sources 30-41.

Throughout this description, communication links from one component to another will be discussed and illustrated. For clarity, the arrows indicate the direction of the communication. The arrows may be understood to indicate either separate, one-way communication links. Alternatively, they may indicate a single communication link that facilitates two-way communication. As would be appreciated by those skilled in the art, the communication link(s) may be a telephone line, a wireless communication link, or the Internet, among others. Data communicated from one component to another can also pass through one or more nodes, which can serve as a local data collection and communication module performing functionality commonly associated with a networked system, such as "store and forward" and other low-level data collection, processing and communication functions.

What follows is a description of exemplary types of information that can be useful in the system, exemplary techniques and methods of collecting that information, and exemplary usages of that information. Because of its far-reaching applicability, to facilitate an understanding, the discussion that follows focuses primarily on the application of the present invention to medical imaging, and particularly medical imaging which involves the use of ionizing radiation, non-limiting examples of which include computed tomography (CT), x-ray, angiography, nuclear medicine, computed radiography (CR), direct radiography (DR), and mammography. However, the scope of this disclosure is not intended to be so limited unless otherwise expressly stated.

As mentioned above, system 10 is designed to collect and utilize both objective and subjective information about a particular medical imaging procedure or set of medical imaging procedures. For purposes of this disclosure, objective information relates to information that is a quantifiable value concerning the procedure itself or the outcome thereof. This would include, for example, patient demographics, study or protocol parameters used to define the performance of the medical device, operational data gathered by the medical device during the procedure, as well as other quantifiable information about the procedure. Objective information can also include knowledge that the system 10 has accumulated about the particular medical devices involved in the procedure. Parameters could include information extracted from the medical device, such as a DICOM conformance statement(s), which may provide insight into the device capabilities and/or limitations that is not gathered during the imaging procedure. To further illustrate this point, examples of objective information associated with a CT imaging procedure could include information such as study or procedure name, study UID, contrast volume used, saline volume used, contrast brand name, contrast concentration, tube voltage, injection flow rate, injection site, bolus timing, syringe type, scan delay, scan region, patient location, protocol name, scanner model and manufacturer, scanner software, radiation dose index parameters such as permutations of CTDI (CT Dose Index) and the Dose Length Product (DLP) or Dose Area Product (DAP), acquisition parameters such as slice thickness, rotation time, image resolution matrix, maS index, etc., as well as information about the age, gender, height, weight, medical condition, heart rate, etc. of the patient. For purposes of this disclosure, subjective information about a particular medical imaging procedure relates to a subjective, or qualitative, assessment of the quality of the result or outcome of a particular procedure. Such information can, for example, take the form of a reviewing technician or physician's opinion about the quality of an image which resulted from an imaging procedure. This is not to say that the qualitative assessment cannot be computer-generated or computer-aided, since the disclosure contemplates that this can occur, such as through a computation of the level of contrast enhancement achieved during a particular imaging procedure. However, the subjective information discussed throughout is focused more on how "good" the result is rather than on what operating parameters were used to achieve these results.

Information sources 30-41 can include one or more conventional medical imaging devices, such as devices used in performing the procedures discussed above. For purposes of this disclosure, a medical imaging device can include the contrast injector system, the scanner system, or a combination thereof, as well as the associated software and user interfaces used to operate the various components. In certain non-limiting embodiments, system 10 can include more than one medical imaging device, more than one type of medical imaging device, and/or medical imaging devices manufactured by different manufacturers. Because medical imaging devices manufactured by different manufacturers, and even medical imaging devices from the same manufacturer but of different generations, often have different reporting capabilities, the system can include multiple means of collecting information from the medical imaging devices to account for such differences in reporting capabilities across different devices.

Information about imaging procedures can be collected from medical imaging devices according to a variety of techniques. For instance, it is well known that medical imaging devices are capable of generating and capturing information about an imaging procedure. By way of example, operational information generated before, during, or after use of the device can be captured and/or stored by the device. For instance, operational information can include data pertaining to the operation of the imaging device that is generated during the operation and captured either in real time or periodically during the procedure. Medical imaging devices can also capture information about the study or protocol parameters used to define the performance of the medical imaging device as well as patient demographics to the extent that this information has been provided to or otherwise made known to medical imaging device. Techniques for collecting, managing, and disseminating information from a medical device include those discussed in U.S. Pat. No. 7,996,381 to Uber et al., which is expressly incorporated herein by reference. In some non-limiting embodiments, information from the medical imaging device is transferred directly to database 20 through an electronic communication link. In other non-limiting embodiments, information from the device is initially sent elsewhere, such as a medical record system, and then later transferred to database 20. Information from the device can also be sent to multiple locations simultaneously, and some types of information, such as contrast usage or radiation dose usage, can be transferred to one location while other information, such as information about scan delay or the injection parameters, goes elsewhere.

A medical imaging device can also be configured to create an electronic study report based on the raw data generated during the procedure. Information captured by the medical imaging device can then be stored in the electronic study report. The use of electronic study reports that comply with one or more industry standard formats is common in medical imaging. Non-limiting examples of electronic study reports include DICOM Secondary Capture Image and DICOM Structure Report Radiation or Contrast Dose Report.

Information sources 30-41 can also include registries 35, repositories, and reporting systems 32 which are commonly associated with medical imaging. These include picture archiving and communication systems 33 (PACS), radiology information systems 31 (RIS), hospital information systems (HIS), electronic health records (EHR), and similar systems and data repositories. These sources typically contain information in the form of images, imaging reports, patient demographics, patient medical history, etc. For purposes of this disclosure, these are referred to as medical record systems. Information can be transferred from these sources to database 20 using techniques known in the art, including those discussed above in connection with medical imaging devices.

Information sources 30-41 can also include workstations located, for example, in the office of a technician or physician, in a reading room 34, or at any other location either on site or off site. A workstation typically includes a computer device which is capable of receiving and transferring data through a network and which has installed thereon software which can be executed to perform a designed task. Workstations can be configured to receive data from any component of system 10, including medical imaging devices, medical record systems, or database 20, to enable the operator to review and/or update the data, and then to transfer the updated data to any component of the system 10. Workstations can be used, for example, to receive an electronic study report from a medical imaging device, to input additional information into the study report, such as a subjective assessment about the result of the study, and then to transfer the updated study report to another component of the system such as a medical record system or database 20.

System 10 is designed to handle each information source 30-41 simultaneously providing data to the database 20. Information can be transferred to database 20 using any technique known in the art for transferring data between components on a network. Information can be obtained by database 20 by querying the information source 30-41 with a request for certain information and allowing the information source to deliver the information in response to this request. Information can also, or additionally, be "pushed" from the information source 30-41 either in real time as the information is generated or periodically in a batch operation. Whether information is automatically pushed or sent only when requested can be information-dependent in the sense that some types of information may be sent automatically while other types of information may only be sent when requested. Rules governing the transfer of information can be determined by a system administrator based upon the particular needs of the system 10 and can be programmed into system 10 at the appropriate location.

The information from each information source 30-41 can be transferred directly from information source to database 20, indirectly to database 20 through one or more intermediary locations, including through one or more other information sources 30-41 or databases, or some combination thereof. For example, certain information obtained from a medical imaging device related to a particular medical imaging procedure can be first transferred to a medical record system, such as PACS 33 or RIS 31, where it can be processed and stored for some amount of time before it is transferred to database 20, while other information obtained from a medical imaging device related to the same medical imaging procedure can be sent directly to database 20.

Information about the same procedure collected from various information sources 30-41 can be combined to form a procedure record using study identification values associated with the information that aids in determining which procedure a piece of information corresponds to. For example, certain information about Study A can be collected from a medical imaging device while other information about Study A can be collected from a medical record system. A procedure record about Study A can be created, and the record can include the information from both information sources. A study identification value associated with the information from the medical imaging device can be matched with a study identification value associated with the medical record system to help in forming the record.

In some non-limiting embodiments, additional information can be added to the output of information sources by passing the information source output through a pre-processor module, which may be contained on a node. For instance, a pre-processor module can be used to add information that would not typically be generated by the information source 30-41, such as location context, including site tags or geo-location tags, and any other desired user-defined data, such as informal names for certain procedures used at certain locations. For example, if a hospital refers to CT scans of the abdomen as "CT Abdominal," a pre-processor can add this field to the output of the medical device. Similarly, pre-processor can add location information (e.g., scan room number) that may not be otherwise part of the information that is output from the information source 30-41. System 10 can also include other intermediate processing components for converting information from information source 30-41 into one or more preferred formats before being transferred to database 20. Alternatively, some or all of the necessary formatting can occur at database 20 or at the information source 30-41 itself.

Database 20 can also be in communication with other similar systems, including systems within the same hospital or systems at other hospitals on a local, regional, national, or international level. In some non-limiting embodiments, database 20 can run on a cloud computing platform. FIG. 4 illustrates various levels across which communication can occur, with the lowest level being represented as a single hospital, a mid level being represented by a collection of hospitals (collectively referred to as an IDN, or integrated delivery network), and the highest level represented by a series of IDNs (e.g., IDN1, IDN2, and IDN3) which each can be composed of a plurality of hospitals (e.g., HOSPITAL 1, HOSPITAL 2, and HOSPITAL 3).

As mentioned above, the invention is designed to collect and compile both objective information about a particular imaging procedure as well some measure of the quality of the results of the imaging procedure. Various techniques are envisioned for collecting this information. These include techniques of collecting information known in the art, including those discussed in U.S. Pat. No. 7,996,381 to Uber, which is expressly incorporated by reference. A desired goal is to develop a robust set of data that includes key pieces of information that can be used by to provide assistance in improving overall image quality through consideration and analysis of the results achieved in past imaging procedures.

In some non-limiting embodiments, the information collection process involves extracting, "mining," or "harvesting," certain pieces of information from the data available from the information sources 30-41. The extracted information can then be used to create a record of the procedure which can be stored in database 20. Data extraction can involve parsing a data set to locate the information of interest, extracting that information, transferring the extracted information to a particular location, and storing that information at the location. With respect to the system described herein, data extraction can take place at any point in system 10, including at information source 30-41, or at database 20 itself, as well as at an intermediate component located between an information source 30-41 and database 20, or between two information sources 30-41, that may be equipped with the necessary hardware and software for performing data extraction techniques.

Data extraction techniques can be adapted to address the various configurations in which information is typically provided by information sources 30-41. This could include developing data extraction techniques that consider the typical structure and/or content of information (e.g., DICOM dose report secondary capture, MPPS, Digital Radiography Dose Report, text, speech, etc.), the types of information typically contained therein (e.g., procedure parameters, quality assessments, scan images, dose reports, etc.), or the source of the data (e.g., a scanner by a certain manufacturer, a handwritten report, etc.). Data extraction techniques that can operate across the widest number of potential formats and sources are preferred. For instance, extraction techniques that are configured to work with industry standards, such as DICOM, and other standards commonly used for handling, storing, printing, and transmitting information in medical imaging procedures, are particularly useful. By way of example, a medical imaging device operating according to the DICOM standard can be configured to record data about the images acquired, beginning time, end time, and duration of a study, as well as total dose delivered, among other information, in the objects of the modality performed procedure step (MPPS). This data can be extracted using data extraction techniques that are based upon a familiarity with the file format and the location of the targeted piece of information within the MPPS objects. As another example, information stored in the objects of a DICOM Structured Report, including radiation dose data, can be extracted by parsing the contents of the Structured Report using known data collection software. There are other techniques of parsing and extracting information from the DICOM objects known in the art as well, and these techniques may be incorporated herein. Data extraction techniques that can be adapted to work across a wide variety of medical devices, including devices from different manufacturers or different versions from the same manufacturer, are also preferred.

One particular data extraction technique involves optical character recognition (OCR). OCR techniques can be used to convert the text or other information contained within a digitized image or document, such as a bitmap image, into a machine-recognizable format to enable the information to be reviewed, analyzed, and potentially extracted. OCR techniques may be useful in the context of this invention to extract pieces of information from, for example, electronic study reports that have been generated during a medical imaging procedure and stored as a digital image in a medical record system such as PACS or RIS. For example, many medical imaging devices can create a static study report, which may be in the form of a secondary capture object that is typically sent to PACS as a digital image. The image may include information about the procedure itself, including the parameters used in the procedure. In a CT procedure, for instance, information about the X-ray tube settings, CTDIvol and DLP, among others, may be contained in a report. Techniques have been developed to extract the static data that is "burned" into the report using OCR techniques. These approaches can also be implemented in the present system to extract information from images generated by or stored in certain information sources. One or more OCR engines that are responsible for performing the OCR techniques may be utilized. The OCR engines can be implemented in the form of hardware and software and can be located anywhere along the path of information flow within system 10. The present system can also be architected such that different OCR engines may be incorporated into the software to perform different OCR techniques. Techniques taught in Wang S, Pavlicek W, Roberts C, Langer S, Zhang M, Hu M, et al. "An Automated DICOM Database Capable of Arbitrary Data Mining (Including Radiation Dose Indicators) for Quality Monitoring" Journal of Digital Imaging (2010, September), which is expressly incorporated by reference, can also be used to "mine" radiation dose data from metadata in imagery kept in a medical record system like PACS.

OCR techniques which are optimized for the specific images or types of images that will be analyzed can also be implemented. For instance, electronic study reports and other documents and images generated in connection with medical imaging procedures typically have a set of common formatting characteristics which are shared among reports, documents, and/or images that are generated by the same medical imaging device or that are generated at the same institution. For example, scanners manufactured by the same company often generate reports that have a common layout and utilize the same character font or set of fonts. Similarly, reports that are generated within the same hospital or other institution often have a common layout and use a common set of fonts. An OCR engine can be developed which applies device-specific or site-specific text processing and extraction rules in order to analyze an image that comes from a particular source. For example, an OCR engine can be designed so that it can recognize the particular character set that is used in reports generated by a particular scanner manufacturer or by a particular hospital. It is believed that an OCR engine designed in this manner can operate with little to no human intervention with accuracy levels approaching 100%.

An OCR engine according to the above can include a font database which contains a confirmed character set where the confirmed character set includes an accurate and pre-defined set of characters that are expected to be contained within an image. The confirmed character set can be prepared automatically by one or more OCR engines and/or it can be manually input. The confirmed character set should have some level of human oversight to ensure that the character identities contained are accurate. Before implementing the OCR engine, one or more training passes can be done with exemplary images to ensure adequate coverage and accuracy and expand or correct the initial confirmed character set as needed. The font database can also be updated periodically to add new characters or correct existing entries based upon, for instance, the past performance of the OCR engine or upon changes to the character sets being used in the input images. In some non-limiting embodiments, updating can occur automatically through a feedback process, as described below. The confirmed character sets contained in the font database should be specific to the information source or information sources which the OCR engine typically encounters and any images which may be contained therein. For example, if the OCR engine is used to analyze images or reports generated by a scanner manufactured by Seimens, the font database should contain at least a confirmed set of those characters typically used by a Seimens scanner. By way of another example, if the OCR engine is being used to analyze images or reports from Hospital X, the font database should include at least a confirmed set of those characters typically used by Hospital X. The font database can contain more than one confirmed character set, and the OCR engine can also work in conjunction with more than one font database.

Once the font database is in place, the OCR engine can be used to analyze a particular image or document by detecting and identifying characters in the image based upon information contained in the font database. In one non-limiting embodiment, a sweeping algorithm is used to identify characters using character raster bitmap patterns, beginning with the widest and tallest characters and continuing down to the smallest cells in the image.

Figure 7:
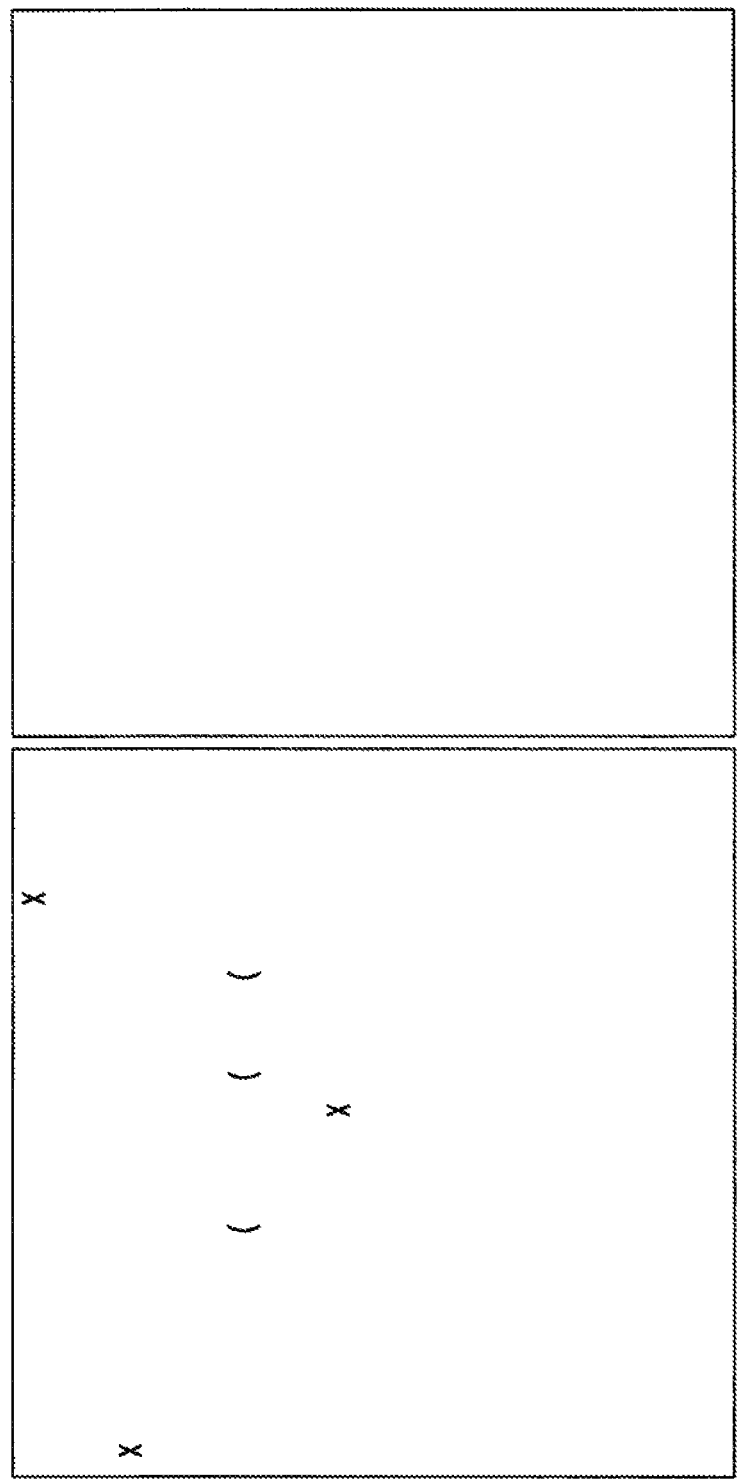
FIG. 7 illustrates a representative example of another aspect of an optical character recognition error correction technique according to the present disclosure.

The OCR engine can also employ one or more quality monitor and/or error correction techniques that can identify potential errors in the analyzed image, including areas of incompleteness, and then take the appropriate steps to correct those errors, including through the use of adaptive correction and residual error correction techniques. One type of a residual error correction that can be used is subtractive masking. Subtractive masking involves a process in which characters which have been identified are "removed" from the image by, for example, replacing the character with the background color of the image. For example, if the image includes white characters on a black background, characters which have been identified through the OCR process can be "removed" by replacing the white character with a black character of equal size and shape. Characters which have not been determined through OCR will then remain visible after the subtractive masking process. A non-limiting example of subtractive masking is shown in FIG. 6, which shows the result of a subtractive masking process. In FIG. 6, the font database is not complete and the subtractive masking produces the image on the right from the image on the left. The unrecognized characters are the following: "( ):x/. The image on the right can then be sent through a residual error correction algorithm. The residual characters can then be extracted and the residual characters can be identified either through one or more other OCR engines or through some level of human review, including a process whereby the residual characters are sent to a human who can then identify the character in question. Once the residual characters have been identified through an error correction process, the image can be updated, and the updated image can be again subject to subtractive masking to confirm whether or not any residual characters remain. In addition, the characters identified through this process can be added to the font database so that, if that same character is encountered in the future, the font database will be able to accurately identify the character based on this newly input value. Thus, the OCR engine can be adapted based on previous outcomes. FIG. 7 shows a non-limiting example of the error correction technique with the image on the left showing several unrecognized characters that have not been "removed" and the image on the right showing the result of subtractive masking after the unrecognized characters have been identified and added to the font database and the image has been again reviewed.

The OCR engine can also utilize a mechanical turking agent for error correction or font database update purposes. The concept of mechanical turking involves coordinating the use of human intelligence to perform tasks that a computer is unable to do. In the field of character recognition, this can include presenting to a human or set of humans one or more characters that were not recognized by the computer. The human or humans then identify the character and the results of this identification can then be returned to the computer and used for future analysis. Mechanical turking is sometimes associated with the concept of "crowd sourcing" in that it involves outsourcing tasks to a group of people who then each perform the task and return the requested information. The OCR engine described above can use a mechanical turking agent to populate a font database through a process of presenting characters that are not part of font database, including residual characters that remain after error correction, to a human or set of humans for identification. The results of the human identification of these characters can then be inputted into the font database.

Figure 8:
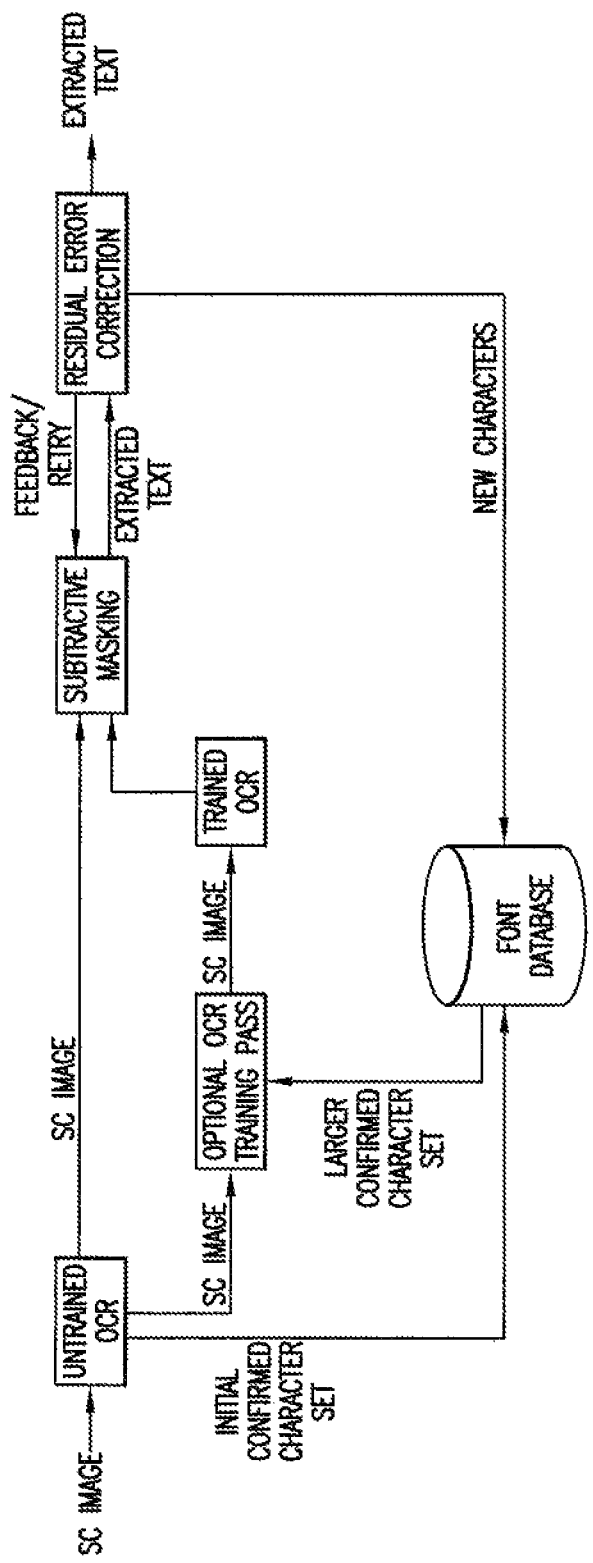
FIG. 8 illustrates a flowchart for an embodiment of an optical character recognition system according to the present disclosure.

FIG. 8 represents a representative workflow of one embodiment of the OCR techniques described above.

The OCR engine can also be adapted to recognize, in addition to characters contained in an image, the structure of the image, including where certain types of information is located within the image. Through the use of image templates and format rules associated with the OCR engine, location context and other information about the recognized characters contained in the image can be appended to the analyzed image. For instance, a particular institution may require completion of a certain form document following completion of a medical diagnostic procedure. These forms may then be converted to digital format (e.g. by scanning) and stored in an image repository. These forms, by their nature, may contain information requested in the form and this information may be located at a pre-determined location on the form. By way of example, a handwritten hospital examination report prepared after completion of an imaging procedure which has been converted into digital format and stored in a hospital database may include a segment of text identifying the radiation dose for that procedure, and this text may be located in a text box located on the right margin of the report, four inches from the top of the report. A template can be developed for this report, where the template is used to identify the location of certain information (e.g., right hand margin, four inches from top of document) and the content of this information (e.g., this text represents radiation dose). The OCR engine can then access this template from a template database, which may be the same or different from the font database, use the template to identify the location of certain information, and apply a set of format rules to append additional information to the analyzed image. Such information can be used to create a record of the procedure with information about the procedure appended thereto, either alone or in combination with one or more data extraction techniques discussed herein. Information extracted using OCR can be transferred to database 20 and used in creating a record of the procedure that can be stored in database 20.

Natural language processing (NLP) techniques can also be employed to search for certain phrases and language that may be contained in a particular digitized image or document and, based on the presence or absence of such language, perform one or more data extraction or information gathering processes. NLP can be applied to electronic study reports, images, or other documents or voice recordings, among other sources of information. In addition, NLP can be applied to images that have been first subjected to one or more of the OCR techniques described above. The system 10 can include an NLP engine containing one or more NLP algorithms and a NLP database that identifies the various phrases of interest. NLP engine can also be configured to include data processing rules that are used to perform some action in the event that certain phrases are determined to be present (or absent) in a particular report, recording, image, etc.

One exemplary use of NLP techniques is to determine whether an examination report for a particular procedure includes language that is indicative of the quality of the result of the procedure. For example, the presence of phrases such as "ineffective," "unsuccessful," or "inconclusive" within an examination report may be indicative of a procedure that produced sub-optimal results. On the other hand, "informative," "successful," or "ideal," may be indicative of a procedure that produced optimal results. The NLP engine could determine the presence of one or more of these phrases and, if so, apply data processing rules to the report. Parsing of the language of such reports in this manner can locate procedures that had poor results, or good results, and the results and corresponding procedures can be labeled accordingly so that they can be more easily located. Information indicative of the quality of the result could also be used in creating a record of the procedure that can be stored in database 20. NLP techniques can also be used to target and extract other information. For instance, information which identifies objective parameter information about a procedure could be located and extracted using NLP techniques as described above.

The knowledge gathered by previously mentioned data extraction and NLP techniques can also be used to enrich the aggregate total information associated with the procedure. The enriched data is then available as input for other additional and potentially new data extraction and NLP processes. For example, the concept of CT Suite efficiency (throughput) can be learned through the data analysis process and then can be used to label the source data. The concept of efficiency could then be analyzed in the context of operator name and/or shift number to derive additional insight—potentially also again enriching the source data, and again making it available for new insight discovery.

NLP and OCR techniques, as well as voice recognition techniques, can also be used to identified and extract information from voice recording.

As mentioned above, another aspect also involves collecting information concerning a subjective assessment of the quality of the result of a medical diagnostic procedure. This information can be collected in a variety of ways, including through the NLP techniques described above. Subjective assessment information can be inputted directly at the point of care, such as at a user interface associated with the medical device which is being used in connection with the procedure. Alternatively, the subjective information could be inputted at a location other than the point of care, such as at a workstation, reading room, or even home office. Still further, subjective information can be computed through an analysis of existing examination reports or images stored in a repository.

Regardless of how the subjective information is collected, this information can be linked up with other information concerning the procedure, including objective information about the procedure to create a record of the procedure which includes both objective information about the procedure and a subjective assessment of the results thereof.

Figure 9:
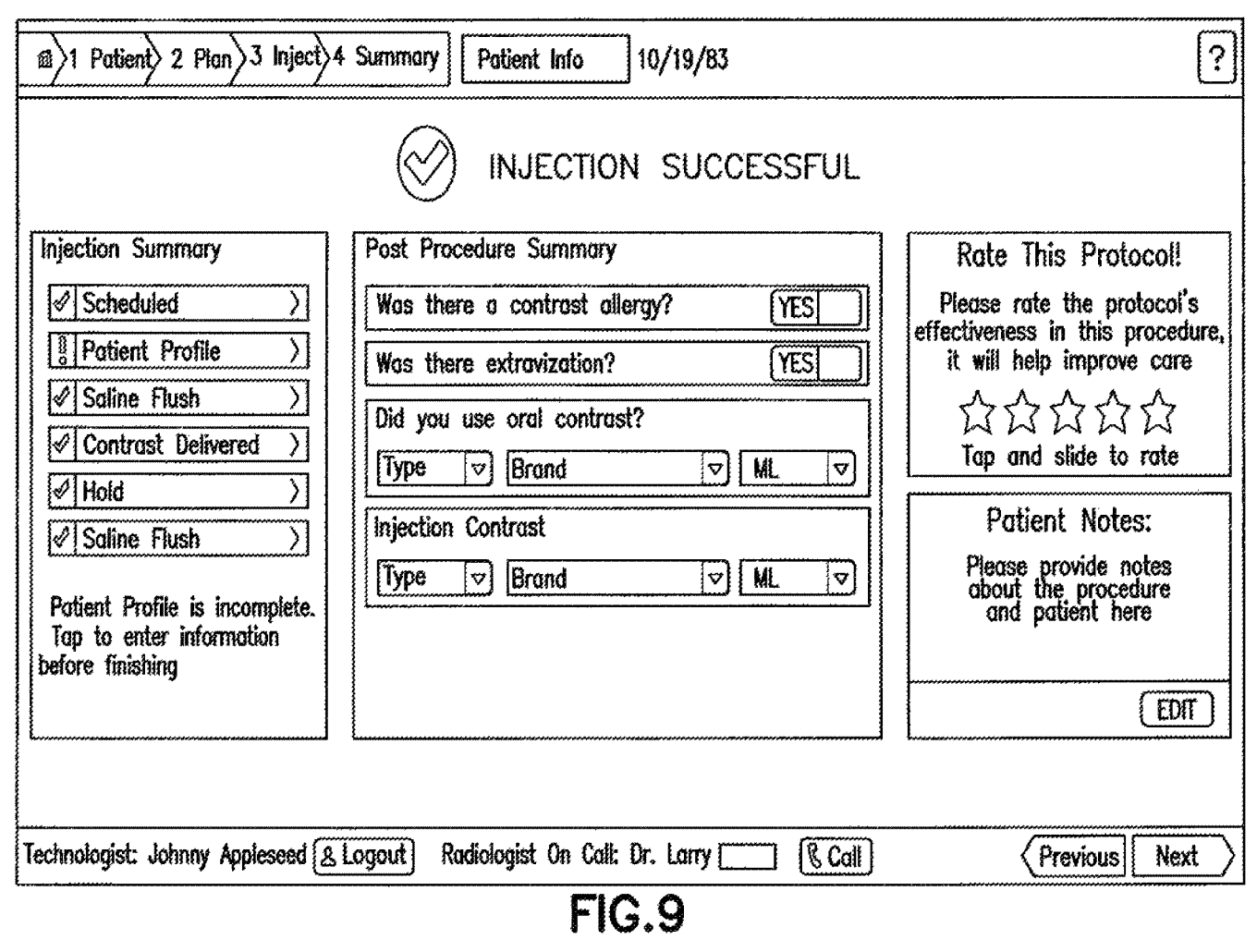

In one non-limiting embodiment, the subjective assessment information can be input at the point of care at or shortly after the procedure is completed, such as at a user interface associated with the medical imaging device. A non-limiting example of the layout of a user interface which would allow for entry of such information is shown in FIG. 9. This has the advantage in that information concerning both the objective and subjective aspects of a particular procedure can be compiled in real time, or near real time. It is also more likely that the subjective assessment will be completed if done so immediately while the procedure is still fresh in the technician and/or physician's mind. In other non-limiting embodiments, the subjective assessment information can be entered at a later time, and can then be linked with the other information about the procedure which might already be stored in one or more locations through the use of a study identification value or other tracking information associated with the particular procedure. For example, a physician can receive at his or her workstation or office the results of one or more imaging procedures that were conducted over a specified time period. The physician can then review the results, enter his or her subjective assessment of each result, and send the assessments either in real time or in batch mode to the appropriate location of system 10, such as database 20, which can be in electronic communication with the physician's workstation or office. This embodiment has the advantage in providing greater flexibility as to where and when the results can be reviewed and assessed. This embodiment also provides the advantage that someone who was not present when the imaging procedure was performed would be given an opportunity to weigh in on the results of that procedure. Multiple reviews of the same result by different persons or by the same person at different times can also be accomplished and the results of each review can be included in the procedure record where they can be presented as an average or kept as separate values associated with each reviewer.

The manner in which the subjective assessment can be entered into the record are in no way limited, so long as the technician, physician or other reviewer is provided a way to express his or her opinion or opinions about the imaging procedure. In one non-limiting example, the results of a particular medical imaging procedure can be reviewed and then "rated" or "scored" according to the reviewer's subjective belief about the quality of the result. For instance, the reviewer can be prompted to assign the result a score from 1 to 5 or from 1 to 10 or using another scale, such as a Likert scale, that may be developed by the particular institution at which the review is being completed or by a standard-setting body. The reviewer can also be asked to score different aspects of the same procedure, such as the contrast quality and/or image quality. Alternatively, or additionally, a result can be "tagged" with a label such as "Optimal" or "Ideal Result," or with data which would be understood to represent such a result, if the technician and/or physician finds the result to be particularly noteworthy. In either case, the quality assessment of a particular procedure can be stored along with other information about the procedure in a manner that allows the results to be associated with the parameters which were used to acquire them. Over time, data on highly rated or tagged results can be accumulated which provides not only the results but other vital clinical/diagnostic data about how those results were achieved, such as the type of study performed, the procedure protocol, patient demographics, etc. In some non-limiting embodiments, procedure records for procedures which achieved highly rated results can be transferred to and stored in a dedicated "best practices" database.

Sentiment analysis techniques to better define and normalize the collected subjective assessment information can also be used. Sentiment analysis is a natural language processing or machine learning technique that attempts to understand the attitude of a speaker or writer. Sentiment analysis can be particularly useful because the review of a study is expressing a judgment. For example, here is a statement from a CT Pulmonary Embolus reading: "This is a limited quality study for the evaluation of pulmonary embolism." One would suspect that this reviewer would not supply the highest quality measure to this study result. Another example could be: "No axillary adenopathy is appreciated." While using language typically associated with a negative review, this is actually a positive statement, in that no swelling of the axillary lymph nodes was observed.

A system can be configured to perform sentiment analysis on different inputs (including text, speech, and scanned documents) to better determine the attitudes that are present in the clinical corpus under analysis. Determining the underlying attitudes and emotional content behind the clinical corpus is a corollary analysis and cross-check for the subjective image quality analysis techniques described herein. For example, if the sentiment analysis reveals an overall negative sentiment polarity but the rating was high, then this may enable the system to flag the rating as questionable.

In addition, sentiment analysis may provide useful information for improving the quality of care if it is conducted on very large data sets. For example, it may reveal hidden beliefs, opinions, or biases that a large group of readers may have, that while widely held, may not be accurate, or may be capable of correction.

In some non-limiting embodiments, the subjective assessment information can be entered into an electronic study report generated by a medical imaging device. In some non-limiting examples, the subjective assessment information can be entered into the electronic study report without altering the existing format of that report. This provides an advantage in that subjective assessment information collection can be easily integrated into existing systems with minimal interruption of the existing workflow. Subjective assessment collection can even be performed using a pluggable and/or vendor neutral software solution which works in conjunction with software that may already exist on the system. Further, continued compliance with recognized file format standards helps ensure compatibility across multiple components of the same system or across different systems.

In one non-limiting embodiment, subjective assessment information can be incorporated into one or more attribute fields in an electronic study report. For example, if a reviewer is reviewing a particular image which complies with the DICOM standard and wants to tag the image as noteworthy, he or she can do so using a specific object within the DICOM format, such as the key object selection (KOS) in DICOM. The key object selection can, in this manner, be considered to serve as a digital "Post It." The key object selection template is intended for flagging one or more significant images, waveforms, or other composite Service Object Pair Instances. Key object selection can contain a coded document title stating the reason for the significance of the referenced objects in the key object selection, an optional free form text comment in an explicitly identified language, and an optional identification of the observer (device or person) which created the key object selection.

Figure 10:
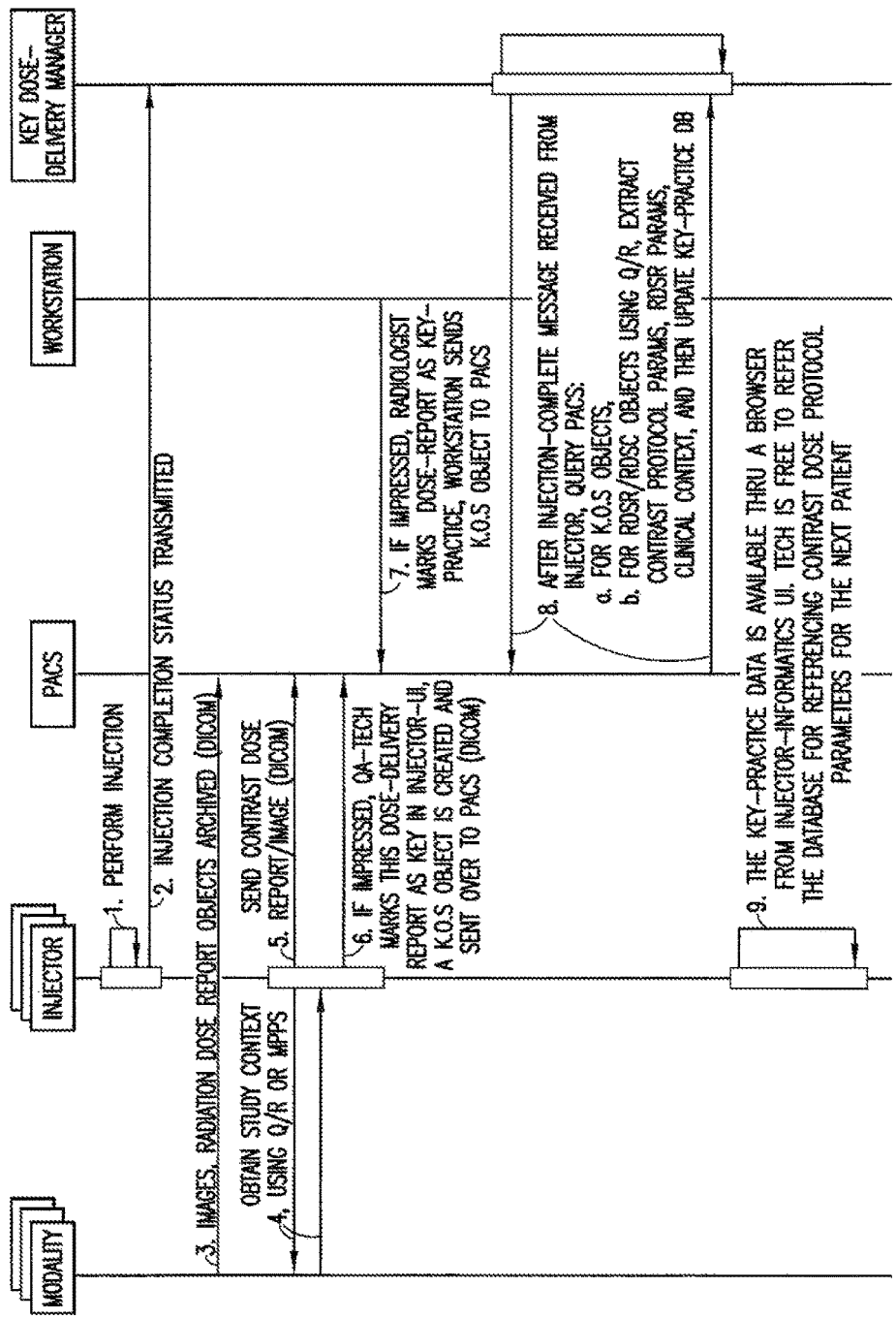
FIG. 10 illustrates a workflow diagram of one embodiment of collecting subjective assessment information according to the present disclosure.
Figure 11:
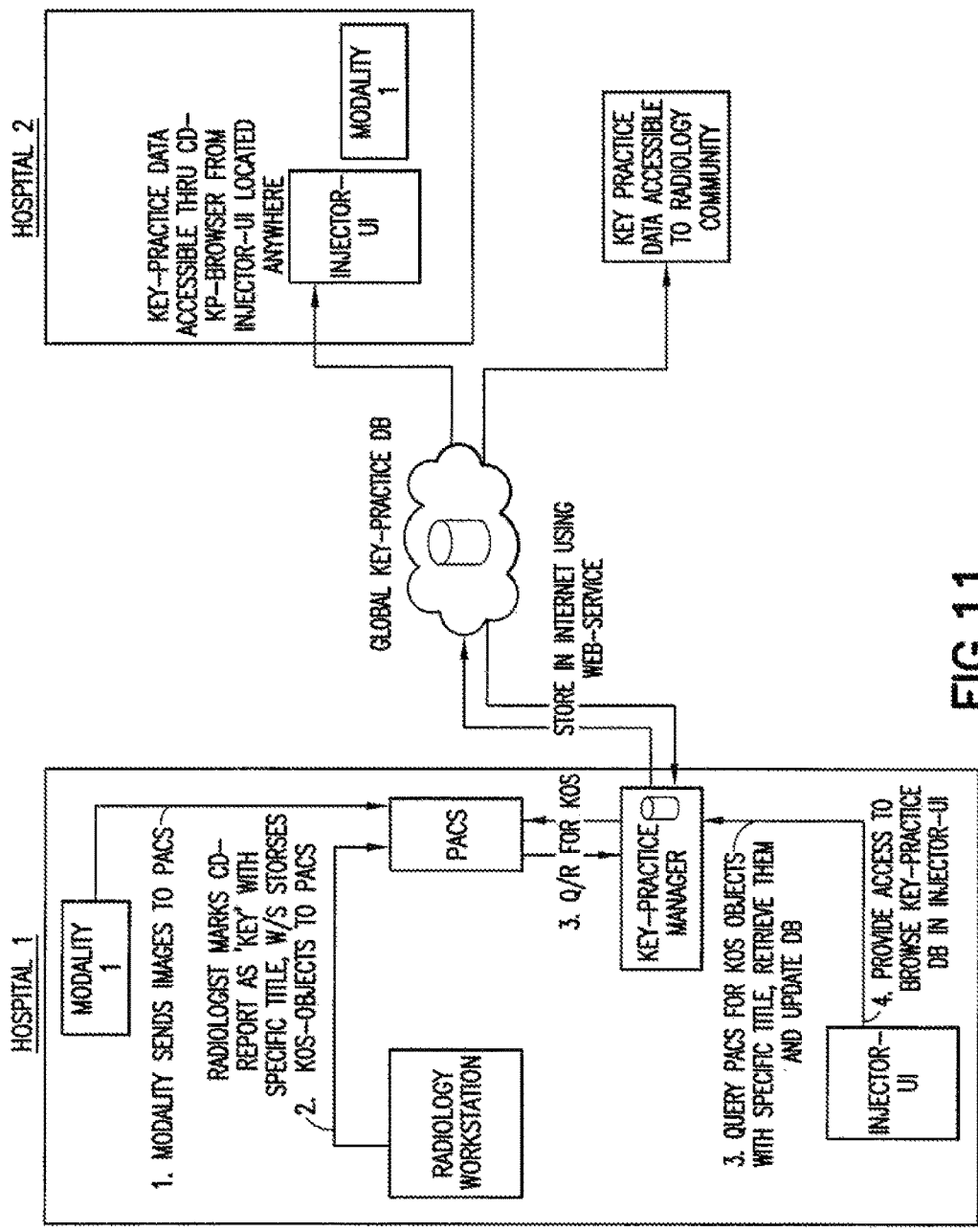
FIG. 11 illustrates a flowchart of the embodiment of collecting subjective assessment information according to FIG. 10.

The above concept is further explained by reference to the following example, which is not intended to be limiting. Reference is made to FIGS. 10 and 11, illustrating the workflow and flowchart for an embodiment of this example, in which the diagnostic procedure in question is a CT scan to patient A. An injection is performed to patient A, patient A's clinical context is obtained from a medical record system such as HIS, and study context is obtained. A contrast-dose report and secondary image capture, both in DICOM format, are created, transmitted, and stored in PACS by software associated with the scanner/injector. A radiologist, at his or her workstation or elsewhere, then accesses from PACS the results of patient A's procedure. If impressed with the results, the radiologist "tags" the report and/or secondary capture image as a "key image" using software installed on his or her workstation to create a key-object document object with a specific document title such as "Of Interest," "For Teaching," "For Research," "Best In Set," etc. These strings can be defined in Context group CID 7010 under DICOM standard Part-16. Alternatively, the tag could be assigned at the point of care through a user interface associated with the CT scanner and/or injector which can be used to create a key-object document object.

The created key-object DICOM document could refer to the report or secondary capture images and is stored in PACS, database 20, or a separate database dedicated to collecting and storing records of procedures that are found to have particularly desirable results. A subsequent query of PACS, or the other source, for key-object instances would lead one to this record and, from the record, one could obtain information about the procedure which resulted in this favorable result, including the injection protocol parameters, radiation dose parameters, and patient-specific clinical and demographic information that is stored in the record. For example, database 20 could query PACS for all key-object instances in order to collect information about these procedures. Such information, including information about the objective and subjective aspects of the procedure, could then be transferred to database 20. Information about the key-practice object, such as the key-practice protocol parameters, could also be submitted to a centralized, secured location accessible through the web.

While the above example relates to the use of the key object selection in PACS, one could envision other similar solutions in which subjective assessment information is stored within existing data format structures already being used in a particular system.

In some embodiments, system 10 can also make a quality assessment determination directly from images obtained as part of the imaging procedure. Such images can include those that are stored in a medical record system such as a PACS. These images may be queried and a copy of the examination images and information moved, using standard DICOM services, to a software module. The software can be configured to perform automated image analysis and extrication of various anatomical structures and also local and global features of the image quality and noise inherent in the data set such as the power spectral density, the standard deviation of noise within sections of the image, and other well-known measures. A particularly useful processing step for assessing quantitative contrast opacification and enhancement makes use of well-known image segmentation and extraction methods, such as seed-growing, level-set, and gradient-descent approaches and those disclosed in United States Published Patent Application No. 2009/0316970 to Kemper et al., to be issued as U.S. Pat. No. 8,315,449, which is expressly incorporated herein by reference, to isolate various anatomical structures in the image data set, for example the descending aorta. Because the level of contrast opacification in anatomical structures is dependent on the scanner and injection parameters when exogenous contrast agents are introduced into the patient, a measure of actual contrast opacification is critical when ascertaining the success of various strategies to optimize and personalize scanning and contrast delivery parameters for individual patients and across patient populations. These methods for extracting contrast opacification can be applied to the image sets. In the instance of assessing the contrast opacification in the aorta, for example, a segmentation and extraction software module can compute the average contrast enhancement along a center-line down the middle of the aorta. A calculation of average contrast opacification in a Region Of Interest around the center-line point and extending to the boundary of the vessel lumen at linear increments (e.g., every 5 mm) along the vessel can be performed. The result of these automated calculations is a vector of contrast enhancement values with dimension determined by the number of increments along the vessel. This vector of opacification points is stored in database 20 and can be associated with the patient and the procedure.

Figure 12:
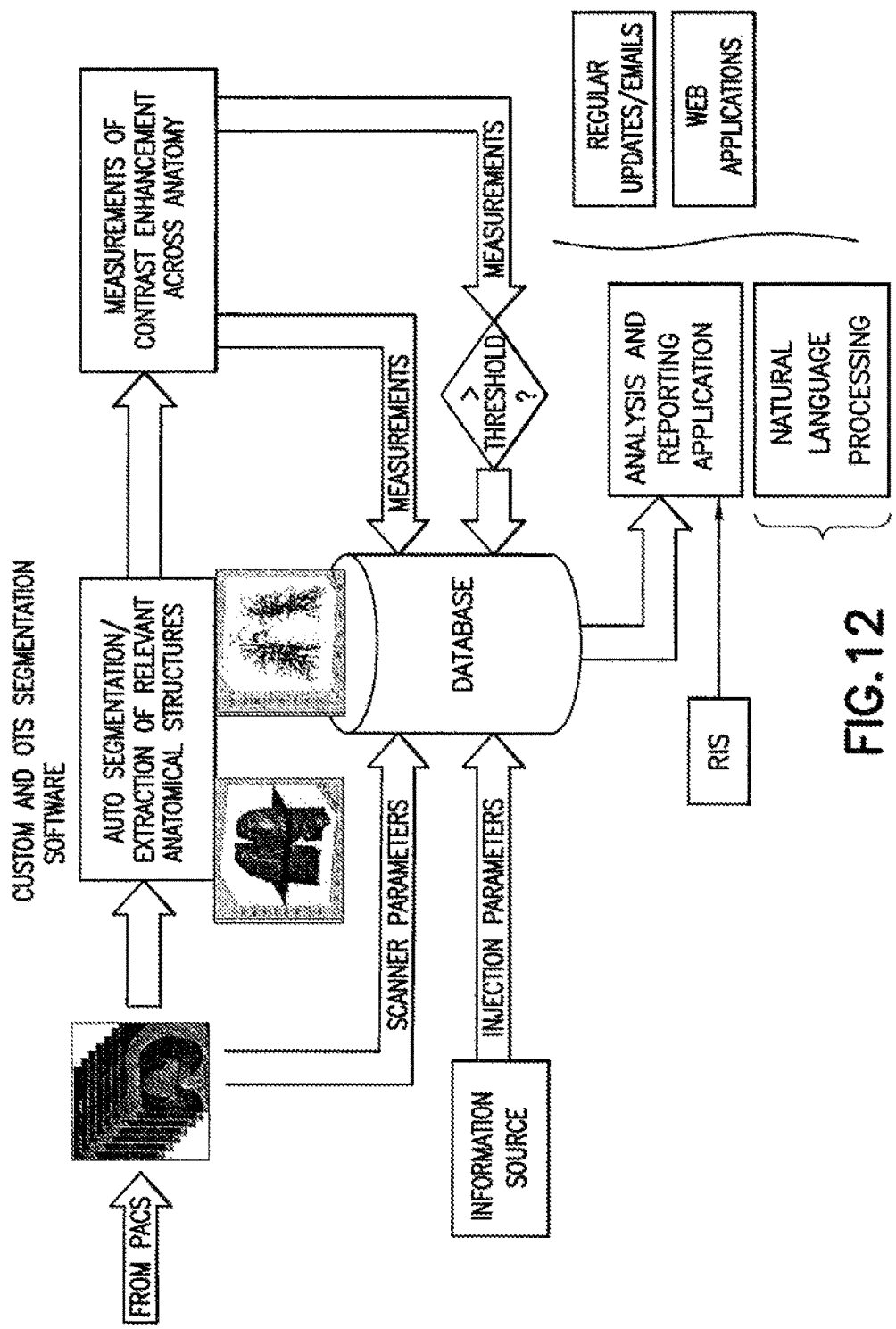
FIG. 12 illustrates a flowchart for an embodiment of an automated method of collecting subjective assessment information according to the present disclosure.

Subsequent use of the opacification vector can be made when determining the relationship among the scanner and injection parameters with patient and examination constraints. For example, it is well understood that at CT Angigophy, the contrast opacification of vascular structures such as the aorta should be at least 250HU to ensure adequate differentiation between clots, constrictions and the lumen of the vessel. A sufficient contrast enhanced CT Angiogram of the chest can be defined by the clinicians at an imaging facility and serve as a subjective measure against which the results of the study can be compared to provide a subjective assessment of the results in accordance with the description herein. One such example of a quality parameter that could be applied would be "contrast opacification greater than 250HU for the entire spatial length of the aorta during the acquisition." A quality metric or Key Performance Index may be defined such that the denominator of the metric is the spatial extent (in cm or mm) of the aorta. The numerator value could be the number of vector data points in which the contrast opacification is greater than 250HU and the larger the ratio the better the study. Across many patients, descriptive statistics of this parameter may be made so as to understand in what percentage of CT chest studies is there "sufficient," according to the defined subjective quality parameter, aortic contrast opacification. A representative workflow to further illustrate the disclosed embodiment of an automated contrast enhancement determination technique is provided as FIG. 12.

The foregoing techniques of collecting information related to the objective and subjective are intended to be exemplary and other techniques may be appreciated by those skilled in the art. As mentioned above, a goal is to populate database 20 with information about not only the objective parameters and other information related to a particular imaging procedure, but also a subjective assessment of the quality of the results of that procedure. Any of the above procedures of information collection can be used in any combination to formulate a procedure record that contains relevant information about the procedures performed and that can be stored in database 20.

Once collected, information stored in database 20 can be used for a variety of purposes to help understand and improve upon the medical imaging process. The system can be configured to allow the information from database 20 to be queried from one or more locations simultaneously. The system can also be configured to be permission based, whereby only certain users can access database 20 and/or update the information within the database. Information stored in the database, or any portion thereof, can also be offloaded to another location, including to a cloud storage system, which can be accessed.

In some non-limiting embodiments, the information collected at database 20 is made available to other components within the system, to other similar systems, and to internal or external registries set up by professional societies or governmental agencies that may be interested in gaining access to the collected information. Information from database 20 can also be hosted "in the cloud" to improve ease of access. In such instances, patient-specific data may be anonymized to protect patient privacy. Analysis applications could be used to access the database information to conduct a variety of studies on the data set, including both patient-specific and patient-neutral studies. Examples include per-patient dosimetry tracking, quality analysis, and trending determinations. The information could also be used to generate alerts when dose index values exceed predefined thresholds. The database information can interact with certain patient information databases, such as those housing hospital or patient records, to generate patient-specific dose index and dosimetry reports. For instance, this analysis can be accomplished following techniques described in U.S. Pat. No. 7,996,381 to Uber et al., U.S. Pat. No. 6,442,418 to Evans, III et al., and U.S. Pat. No. 7,933,782 to Reiner, each of which is expressly incorporated herein by reference.

Results of these prior studies can be presented in a manner that can be easily browsed and/or filtered based on parameters of interest.

In some non-limiting embodiments, information from database 20 can serve as the source data for a data reporting and analysis application. The data reporting and analysis application can be accessed using a computer and can be in the form of software residing on the computer, though it could also reside on a central server or a centralized cloud location and be made accessible through the web as well. Information from database 20 can be imported into the data reporting and analysis application and the application can then be used to parse, arrange, and present this information in a form that is more readily understandable by a user, as well as to generate reports based upon this information. For example, the application can parse the information received from database 20 and populate a plurality of fields which have been pre-defined by the user. The application can then be used to sort, filter, present and/or analyze this information in a manner requested by a user in order to provide the user with additional insight into the information that has been collected and stored at database 20 and enable the discovery of connections in the information that may not be otherwise known or appreciated. In one non-limiting embodiment the data reporting and analysis application can be implemented using a macro-enabled Microsoft Excel file or a file from a similar spreadsheet or database analysis program.

The application is particularly useful in analyzing and organizing objective information that has been collected regarding a series of diagnostic procedures performed by one or more medical devices. As described above, objective information can include quantifiable information about the particular procedures, including the parameters and protocol information input into the medical device as well as the operational information generated during performance of the procedure.

While the data reporting and analysis application can be configured to work with information related to any type of medical diagnostic procedure, the following discussion refers to CT imaging as a non-limiting example.

Figure 13B:
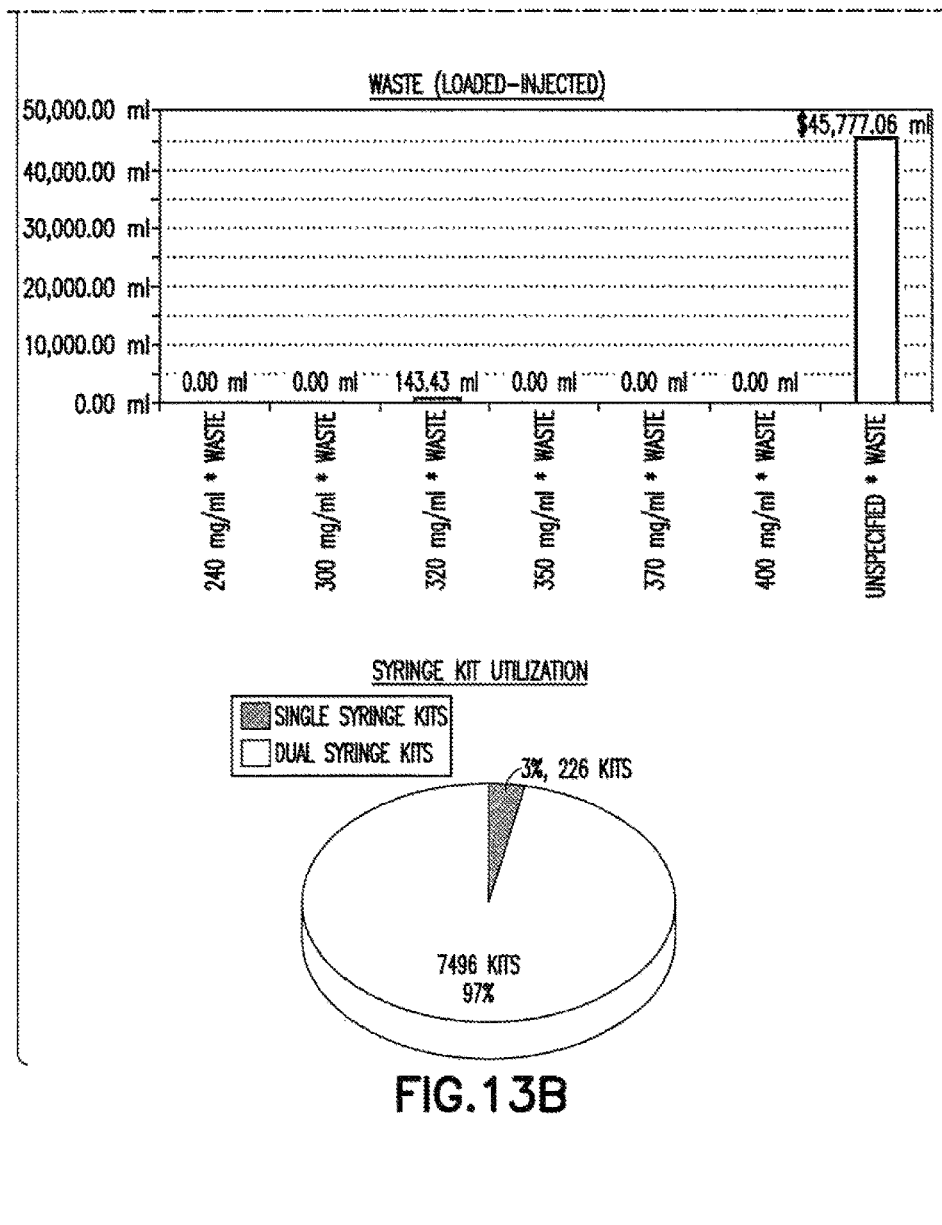
FIG. 13 illustrates a representative format in which information can be presented using a data analysis and reporting application according to the present disclosure.
Figure 13C:
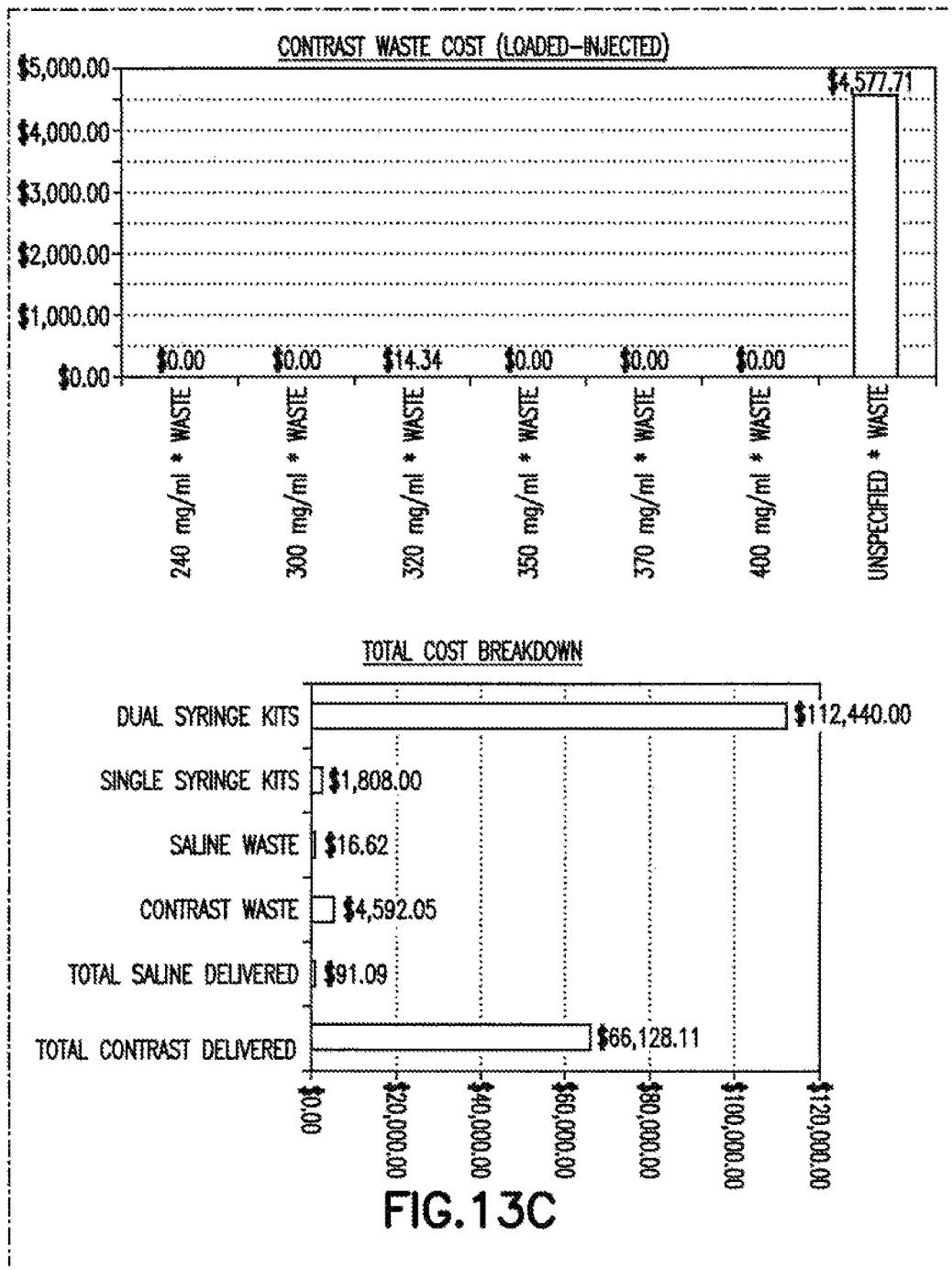

For CT imaging, the procedures application could be used to present in a tabular or graphical view basic metrics about the procedures such as, for example, the amount of contrast or saline delivered, the amount of contrast or saline that was wasted, and the number of syringe kits used on a per device basis or over across a range of devices. Calculations could then be performed using this information to provide, for instance, utilization or cost information, such as the overall volume and cost of the contrast media injected, or wasted, by a particular device or by an entire institution. FIG. 13 illustrates a representative format in which this information can be presented, in both tabular and graphical form. Virtually any type of information stored in database 20 can be presented by the application in a similar manner.

The application can also be used to develop a variety of intelligence reports from the source information. For example, the application can be used to perform a side by side comparison of the information related to different procedures in order to more readily understand differences between the procedures, including the results thereof. This application could also be used to assess the differences between different protocols, including a comparison of the average procedure metrics associated with different protocols. Information which may be included in the report could include such objective information as the number times a protocol was used, the average volume of contrast usage and contrast waste, and the average flow rate of the fluid injection. In addition, information about the result of the procedure could be presented as well, including a subjective assessment of the result. FIG. 14 illustrates a representative format in which this report can be presented.

By way of another example, the application can be used to determine the extent to which the same procedure was performed, or at least initiated, multiple times on the same patient. Gaining insight into the details of such repeat procedures can be an important step in limiting the frequency with which this occurs. For example, having identified an occurrence of a repeat procedure, the user may be able to identify what necessitated this, and take appropriate steps towards ensuring it does not happen again in the future. In the context of CT studies, a repeat injection analysis report can identify which CT studies had multiple injection procedures performed. The report can be generated by determining, based upon an analysis of the objection information provided from database 20, which injections share the same study identification value. The application can then generate a report which provides to the user in a visually perceptible form key information about these repeat procedures, including an itemized list of each injection that was associated with that study, the injection start date and time, injection termination status, volume of fluid delivered, peak pressure, study description, patient ID, accession number, patient name, suite name, number of syringes used for the study, or any similar pieces of information. Information in the report can be provided to the application from database 20 where it can be parsed and populated in the appropriate field of the report. FIG. 15 illustrates a representative format in which this information can be presented.

Figure 17:
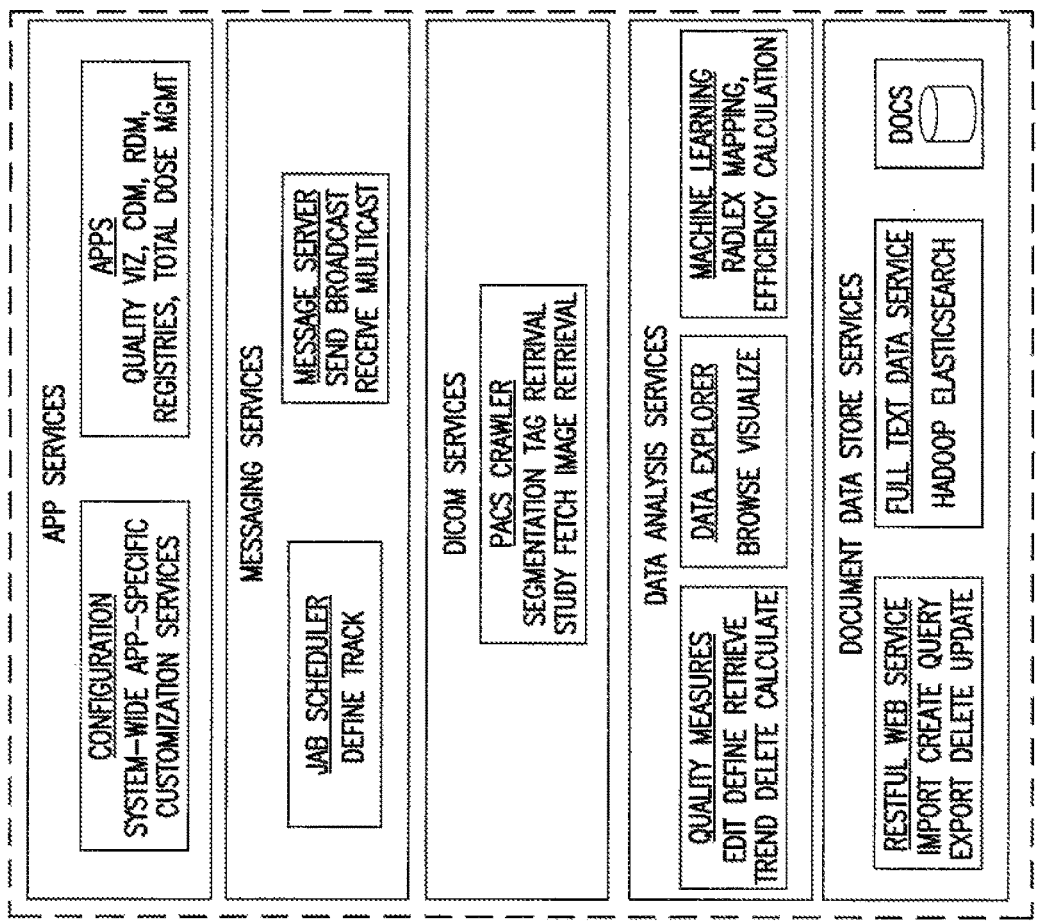
FIG. 17 illustrates a representative stack of information services, technologies and software systems for enabling the collection, persistence and distribution of information according to the present disclosure.

By way of another example, the application can be used to compare information about various complementary protocols. For example, a CT imaging procedure typically includes both a scan protocol and a complementary injection protocol. Based on information about the various procedures that is stored in database 20, the application can analyze this information and present the results in a manner that shows, for example, which injection protocols were used most often with a particular scan protocol, or vice versa. From this, the user can gain an understanding as to what protocols are most commonly used for specific study types. It also allows a user to uncover mismatches between injection and scanner protocols. FIG. 16 illustrates a representative format in which this information can be presented. FIG. 17 illustrates a representative stack of information services, technologies and software systems for enabling the collection, persistence and distribution of information as taught herein.

Figure 18:
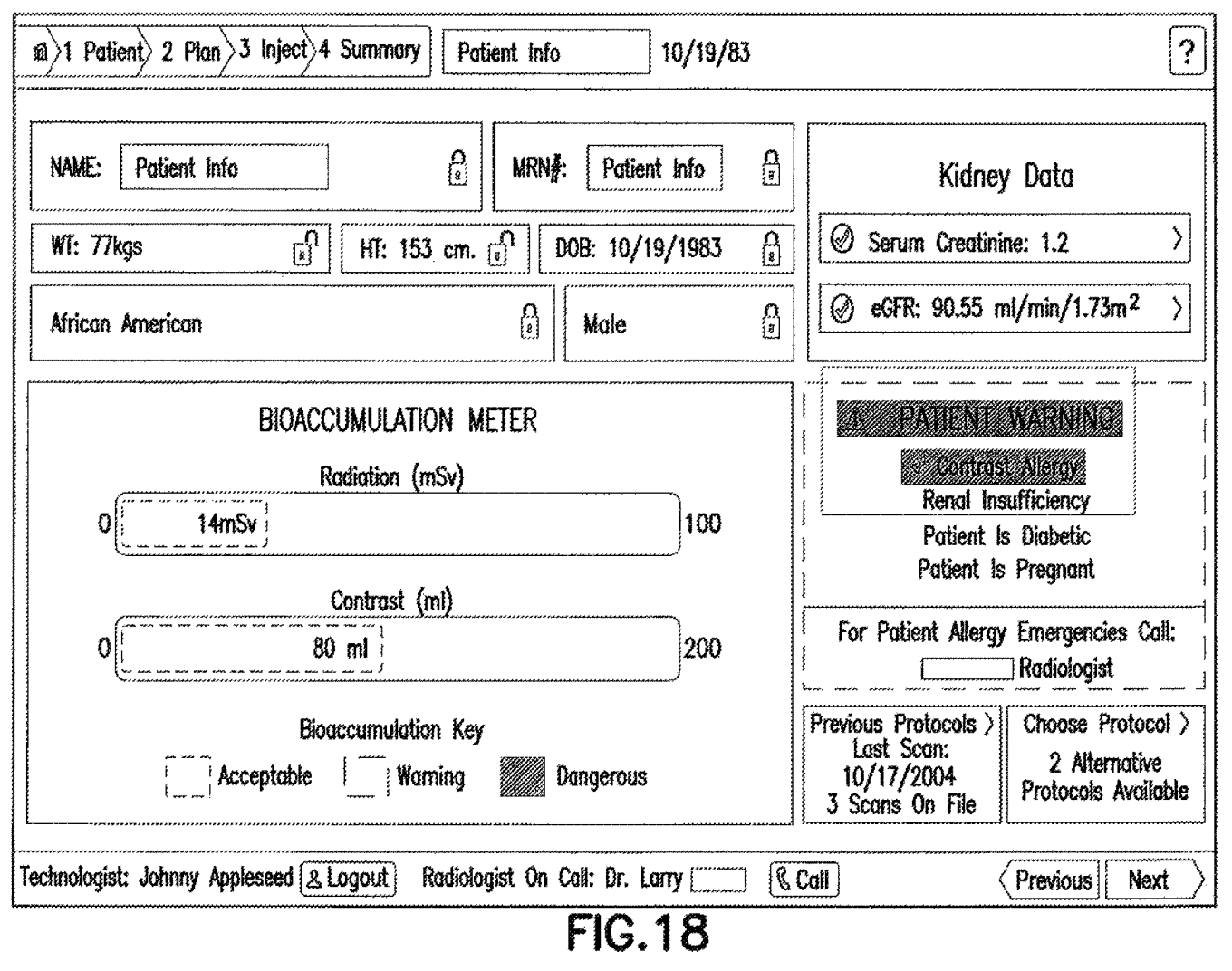

In another aspect of the invention, a user display and interface in operative communication with a contrast delivery system may be used to inform a scanner operator about previous visits the patient had, such as whether there were any difficulties with the scan, whether there were any adverse reactions, and what the patient's aggregate exposure to contrast agents and ionizing radiation over a selectable time period has been. This information may be used to alter the methods for determining the optimal imaging data set for the patient on the present visit. As exemplified in the non-limiting embodiment of the display shown in FIG. 18, the operator of the imaging and injection system may quickly review patient allergies, previous imaging protocols, and also ask for assistance from the on-call radiologist who may be linked to the contrast injection system's communication system through a messaging system, such as Microsoft Corporation's Lync technology, or Google Corporations talk technology.

Figure 19:
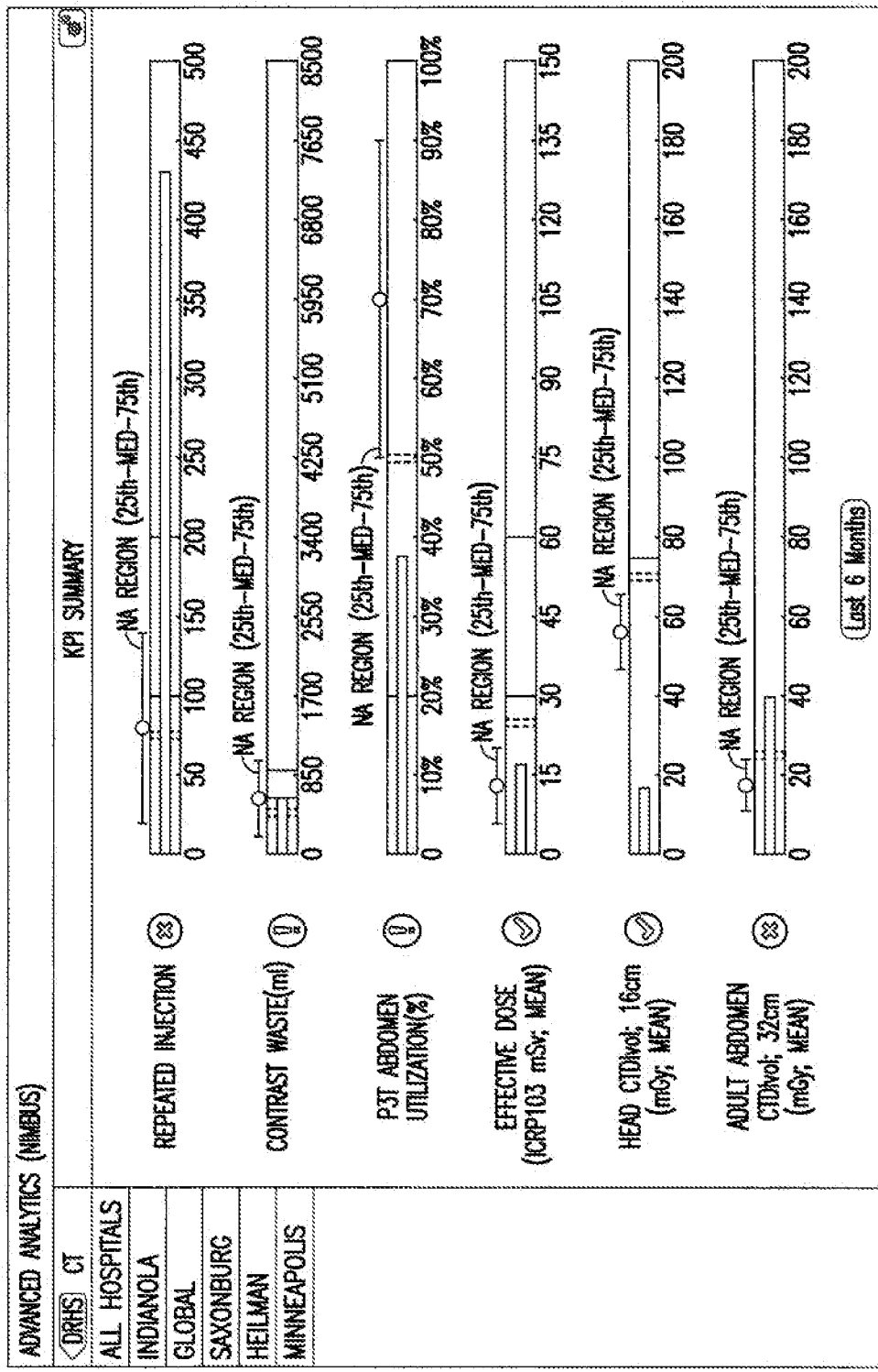
FIG. 19 illustrates a representative example of a user display and interface for presenting information according to the present disclosure.

FIG. 19 represents a representative example of a display which can present aggregated objective information (e.g. operational information) and subjective assessments as collected by the system described herein. Display can also include a facility for displaying performance metrics relative to regional or nationally aggregated values. These data could be used to understand the performance of the department, facility and health system over a period of time and also in comparison to external benchmarks.

In other non-limiting embodiments, the information collected can be subject to further analysis in order to understand and correct how certain objective parameters about a procedure affect the subjective quality of the procedure results. Collecting and storing information about the objective and subjective aspects of a procedure according to the methods and techniques described herein enables the system to continuously improve the quality of the procedure results by continuously monitoring and analyzing the objective information which led to the highest quality results.

One non-limiting embodiment relates to the computation of the effect of scan delay on the quality of the results of different imaging procedures.

For imaging modalities in which a bolus of contrast agent is injected, the delay between the injection of the bolus (both the start and the finish) is a critical parameter for determining physiological function, disease states and the optimal temporal window for visualization of vascular structures (at CT, MRI, Ultrasound, nuclear medicine modalities). The contrast agent bolus is used as tracer, in effect, to determine attributes of the diseased or healthy organism. If a scan is initiated too early, erroneous diagnostic information may be produced and likewise for when scan delays are too long. In simpler cases, the inappropriate timing of the bolus relative to the scan acquisition may produce uninterruptable data sets. A further challenge to contemporary medical imaging practice is that advances in scanner system technologies has shortened the time needed to acquire a full diagnostic data set. This is typically true for all imaging modalities—MRI, ultrasound, nuclear imaging and particularly CT scanning. It is not uncommon to acquire a full imaging data set with the latest CT scanners in less than one second. These very short scan acquisition times underscore the criticality of timing the scanning with the arrival and passage of the contrast bolus and its distribution in the body. Also, advances that offer multiple means to gate and trigger the scanner relative to some physiologic event, such as the heart's electromechanical cycle, make possible that two patients scanned sequentially may have drastically different scan delay and timing considerations.

Figure 20:
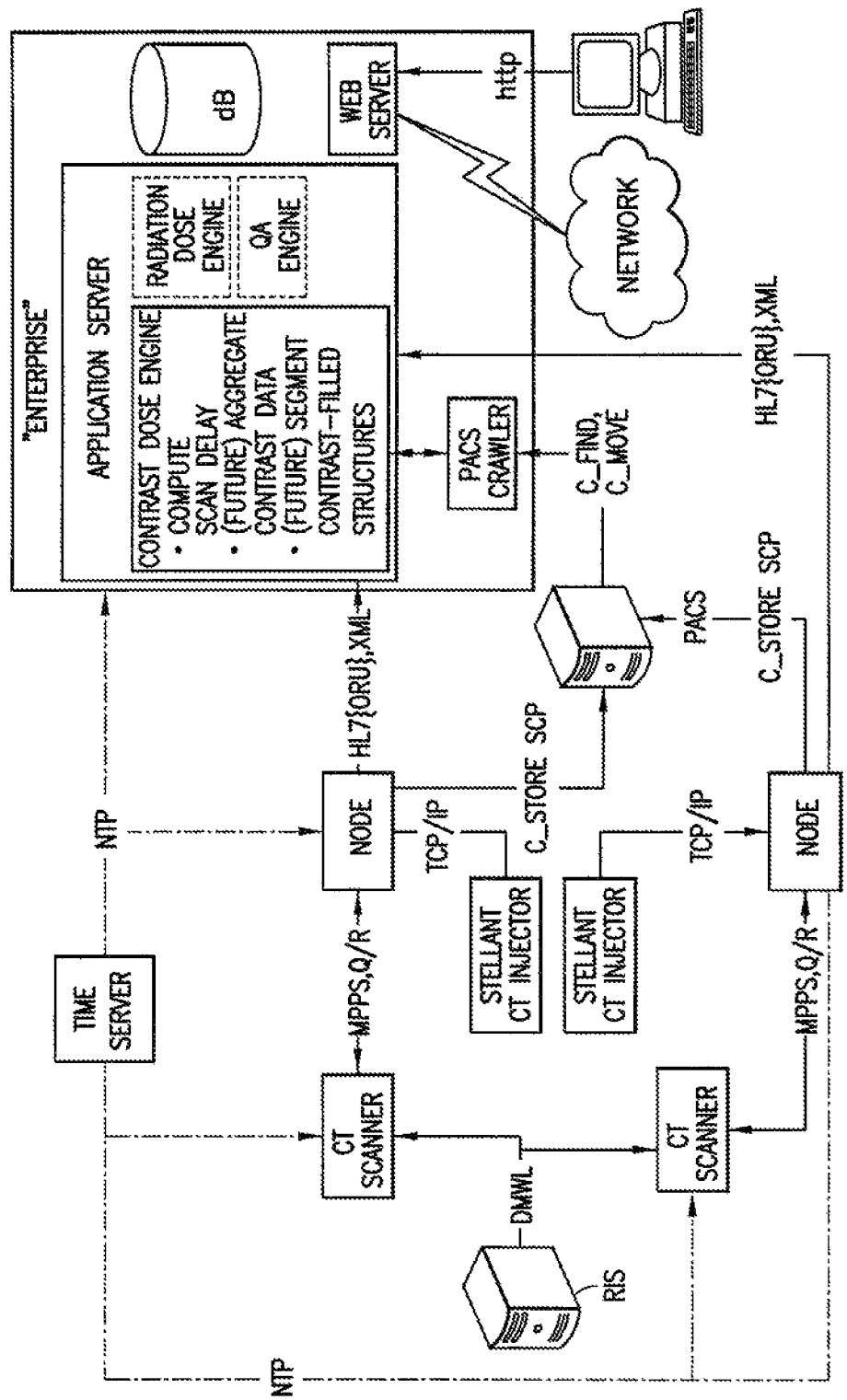
FIG. 20 illustrates a flowchart for an embodiment of computing scan delay according to the present disclosure.
Figure 21:
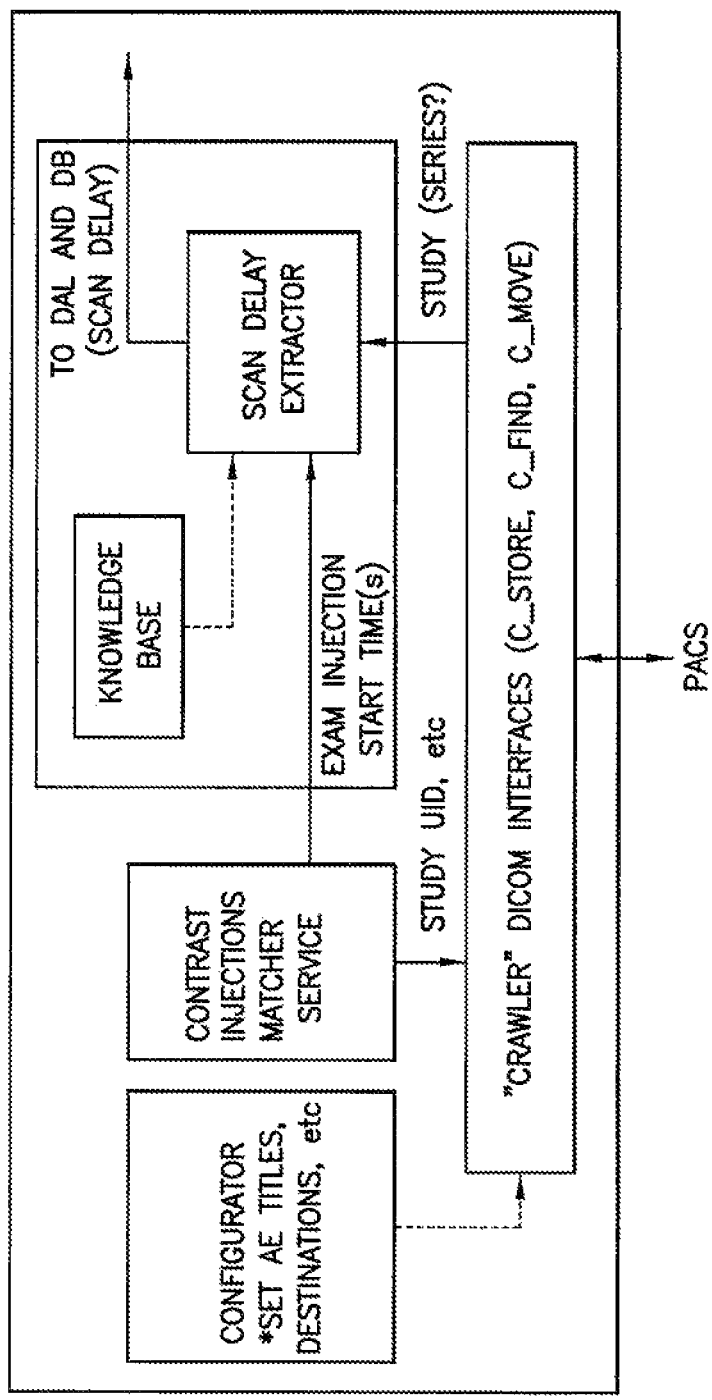
FIG. 21 illustrates another flowchart for the embodiment of computing scan delay of FIG. 22.

The following methods may be used to compute the delay by using image data, operational parameters of the injection system, and a synchronized time base. Assuming the injection system and the imaging system share a common timebase, such as can be achieved by the usage of time servers on a TCP/IP network (either by using the NTP or NNTP protocols), information about the injection start and stop times for an injection system can be collected at injection system and these values can be transmitted to database 20 upon completion of the study. A software agent can also query the images for the patient's study when they are successfully transmitted to a medical record system such as PACS. The software agent can traverse the study data from the acquired image. Preferably, the software agent can exclude any non-primary or "secondary" series of images. Information about the scan acquisition is often stored in the attribute fields of the image. For instance, the DICOM standard requires the inclusion of "Scan acquisition" in the metadata of each primary diagnostic data set (DICOM attribute tag (0008 0032)). Using this information, the software can then compute the difference between the acquisition time of the images and the start and stop time of the contrast injection and this information can be stored in database. Scan delays calculated for each series of images can then be stored in database and can be referenced when retrospective analyses are done on the data to determine the quality of the results of the procedure. If a study is deemed poor, for instance, the radiologist may be asked to consider what scan delay was used. This knowledge can then be used in the aggregate for determining best-practices and for establishing protocols or the ideal scan and injection parameters for a future procedure of a patient who may have had multiple studies in the past which are stored and made accessible through the system. A further illustration of the concept of calculating scan delay is shown in FIGS. 20 and 21.

In other non-limiting embodiments, the collected information can be used to help develop parameters to use for a future imaging procedure. For example, a physician interested in developing an imaging protocol for a particular patient may access database 20 to search for information about other procedures which involved patients of similar demographics and which exhibited high quality results. The physician can then use information about these past studies, along with the knowledge that these past studies resulted in optimal image quality, in deciding the preferred protocol parameters for the upcoming study. This suggested protocol, based on past results, can also be modified using, for example, other available protocol generating techniques, including the modeling techniques disclosed below. Database 20 can also serve as, or be integrated into, a central protocol management application in which procedure protocols for a plurality of devices within and across an institution are stored, labeled, and configured, and then delivered to any devices that subscribe to these protocols.

For example, a physician may query database 20 for information about patients having certain demographics, and specifically request only information about those procedures in which a high quality image was achieved. In one non-limiting embodiment, this query could request only those studies that have been marked as "key practices" using the key object selection technique described above, or a similar technique, or the query could be directed to a "key practices" database which has been populated with only the records for procedures that achieved some threshold quality measure. The physician will then receive, in response to this query, information about procedures that involved a similar patient and which produced optimal results. This information could serve to inform the physician as to the best procedure parameters and aid in the development of a more effective protocol thereby reducing the chance of having to repeat the procedure. The physician can use this guidance in developing the appropriate protocol for the patient at issue.

In some non-limiting embodiments, system 10 can be used in conjunction with known protocol prediction modeling software which may be running on protocol management application to simulate potential contrast enhancement outcomes and the impact of scan timing and other objective parameters on image and outcome enhancements for that patient. Such other models include those developed by Bae and set forth in K. T. Bae, J. P. Heiken, and J. A. Brink, "Aortic and hepatic contrast medium enhancement at CT. Part I. Prediction with a computer model," Radiology, vol. 207, pp. 647-55 (1998); K. T. Bae, "Peak contrast enhancement in CT and MR angiography: when does it occur and why? Pharmacokinetic study in a porcine model," Radiology, vol. 227, pp. 809-16 (2003); K. T. Bae et al., "Multiphasic Injection. Method for Uniform Prolonged Vascular Enhancement at CT Angiography: Pharmacokinetic Analysis and Experimental Porcine Method," Radiology, vol. 216, pp. 872-880 (2000); U.S. Pat. Nos. 5,583,902, 5,687,208, 6,055,985, 6,470,889 and 6,635,030, the disclosures of which are incorporated herein by reference, as well as modeling techniques set forth in U.S. Pat. No. 7,925,330 to Kalafut et al., United States Patent Application Publication Numbers 2007/0213662 to Kalafut et al., 2007/0255135 to Kalafut et al., 2008/0097197 to Kalafut et al., 2010/0030073 to Kalafut, 2010/0113887 to Kalafut et al., 2010/0204572 to Kalafut, and Published PCT Application Numbers WO/2006/058280 to Kalafut et al., WO/2008/085421 to Kalfut et al., and WO/2006/055813 to Kalafut et al., the disclosure of each of which is incorporated herein by reference and made a part hereof. The system can also enable the planning and simulation of image enhancement based upon "what if" scenarios using device parameters such as tube voltage, maS (coupled with noise figure), slice thickness and other attributes of the device. While the technologist may change or alter parameter values as he or she sees fit, the modeling enabled at least in part by the information collected in the present system serves as a good baseline.

Information about subsequent procedures, including both objective information about the procedure and subjective information about the results thereof, can then serve as inputs into the system to further inform future studies. This concept is described in certain aspects above and is further illustrated by reference to the following non-limiting examples which describe the workflow of a closed loop system using information that may be contained in database 20 according to the present invention.

EXAMPLES

One medical imaging procedure that has proven to be particularly challenging for imaging clinicians to consistently perform is CT imaging of the pulmonary arteries after the injection of iodinated contrast material to rule in or out the presence of thrombus or clot. The image acquisition should ideally occur during the first-pass of the contrast bolus through the pulmonary arteries and, thus, there are only seconds between the initiation of contrast agent delivery and scan acquisition. If the scanner operator waits too long to scan, the contrast bolus will have migrated out of the pulmonary arteries and the resulting images will have insufficient contrast necessary to render a diagnosis. If the operator scans too early, the contrast bolus is still in the peripheral veins. Factors affecting the transport of contrast through the pulmonary vessels include the cardiac function of the patient, the age of the patient, pulmonary insufficiency, and other patho-physiological patient factors. Many patients who undergo CT to test for clot have multiple studies. The radiologist responsible for determining the appropriate scanner and injection protocols for an individual patient may use the methods of this invention to recall prior subjective and objective metrics of past exams. If the patient had very poor study outcomes on previous imaging exams, an analysis of the factors associated with the poor quality studies may be done by the system or with manual intervention by the radiologist. The radiologist might, for instance, notice that because the patient has very low cardiac function, that on the upcoming examination the technologist should perform a test bolus injection of contrast to determine the actual propagation time of contrast into the patient's pulmonary arteries. The radiologist may also proscribe a scanner protocol that exposes the patient to a minimal amount of radiation because the patient has had 10 CT studies over the past 12 months. These notations would be placed into an order that the technologists running the scanner can review. All of the information and decision process used by the radiologist for this case, including any results of the scan being performed, would be persisted into the system for future review and enhancements through information gathering methods as described herein.

Another challenging medical imaging examination is the detection, staging and assessment of hepatic carcinomas. At both CT and MRI, the acquisition of multiple sets of scans is necessary to ascertain and differentiate various types of tumors from benign cysts or other structures. These exams are referred to as multiphase and sometimes "dynamic" studies because the contrast distribution and absorption into diseased and healthy tissues changes over various cycles of the contrast agent circulated throughout the vasculature and organs. A scan is often made of the liver and other organs prior to the arrival of a bolus of contrasting agent. Subsequent to this acquisition, a set of data are collected during the "first pass" of the agent during the so-called arterial phase. Later, a scan is made during the temporal period in which the contrast agent is transported into the liver via the portal vein (the so-called "portal phase"). Lastly, one or more scans may be made minutes later to determine how the contrast agent is distributed. Certain tumor types attenuate differently at these phases of circulation—they appear as hypo-intense or hyper-intense with respect the background of the parenchymal tissues at the arterial and portal phases for instance. If the scans are made too late or too early, the appearance of the tumor may be difficult to ascertain. Furthermore, when quantitative methods are used to determine the area or volume of the tissue using WHO and RECIST criteria systematic error may be introduced into these metrics if the contrast opacification pattern in the tumor and the surrounding tissue is not consistent and reliable. The methods taught herein may be used in these cases to better track, plan and optimize the scan acquisitions relative to the injection of contrast, the settings of the scanner and attributes of the patient, and information learned can be added to database 20 for further use.

In MRI hepatic imaging, the use of contrast agents comprised of gadoxetic acid coupled with chelated gadolinium atoms for instance and that bind preferentially to hepatocytes is becoming clinically routine. It is well known, however, there is variability in the contrasting enhancement patterns using these agents as a function of the injection protocol, the pulse sequences used, and most importantly patient attributes. It is believed that certain genetic variations in patient (in particular proteins that affect the function of the organic anion transport mechanisms in the liver) may cause very different enhancing patterns in diseased and healthy patients. The database of prior imaging results and information about the quality of those results as taught herein could be used to help ascertain better imaging strategies for these patients. If there are data feeds from genomic and proteomic information systems, these data can help inform the radiologist protocoling a patient when these contrasting agents are proscribed. Moreover, information learned from the results of such studies can then be added to database 20 to assist in ascertaining better imaging strategies for future patients.

Although the present invention has been described in detail in connection with the above embodiments and/or examples, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

The invention claimed is:

1. A method of collecting and utilizing information relating to medical imaging procedures, the method comprising:
    collecting information about a plurality of medical imaging procedures from a plurality of information sources, wherein the information collected for each of the medical imaging procedures comprises objective information about the medical imaging procedure, including at least information about parameters of the medical imaging procedure and information about a patient that underwent the medical imaging procedure, and a subjective assessment of a result of the medical imaging procedure, wherein the subjective assessment of the result of the medical imaging procedure comprises an individual's opinion of quality of the result of the medical imaging procedure;
    forming a plurality of procedure records, wherein each of the procedure records corresponds to one of the medical imaging procedures, and wherein each of the procedure records comprises at least the objective information about the medical imaging procedure and the subjective assessment of the result of the medical imaging procedure,
    storing the procedure records in a database, wherein the database is in electronic communication with at least a portion of the information sources;
    receiving demographic information about a subject patient;
    accessing the database;
    determining a suggested protocol comprising at least operating parameters of a medical imaging device, wherein the suggested protocol is determined based on a consideration of the demographic information about the subject patient and the objective information and subjective assessments contained in the database, and wherein the medical imaging device comprises a user interface;
    presenting the suggested protocol on the user interface of the medical imaging device in a visually perceptible form;
    performing a medical imaging procedure on the subject patient by operating the medical imaging device in accordance with the operating parameters of the suggested protocol or a modification thereof;
    entering into the user interface of the medical imaging device a subjective assessment of a result of the medical imaging procedure performed on the subject patient, wherein the medical imaging device generates an electronic report of the medical imaging procedure, and wherein the subjective assessment of the result of the medical imaging procedure performed on the subject patient is entered into and stored as part of the electronic report; and
    receiving the electronic report generated by the medical imaging device.

2. The method of claim 1, wherein the information sources include a plurality of medical imaging devices.

3. The method of claim 1, wherein the information sources include at least one medical record system comprising a digitized image or document that is associated with one of the medical imaging procedures.

4. The method of claim 3, wherein collecting information from the at least one medical record system comprises extracting information from the digitized image or document using at least one of optical character recognition and natural language processing.

5. The method of claim 4, wherein the information is extracted from the digitized image using optical character recognition.

6. The method of claim 5, wherein the optical character recognition is performed using an optical character recognition engine comprising a font database, wherein the font database comprises font characteristic information that has been specifically adapted for use with the digitized image.

7. The method of claim 6, wherein the optical character recognition comprises a residual error correction process in which one or more errors that have occurred during the optical character recognition are detected and corrected and information about the errors is transferred to the font database.

8. The method of claim 4, wherein the information is extracted from the digitized image or document using natural language processing.

9. The method of claim 8, wherein the natural language processing is used to identify language within the digitized image or document that is indicative of the subjective assessment of the result of the medical imaging procedure.

10. The method of claim 1, wherein the information sources include a plurality of medical imaging devices and at least one medical record system.

11. The method of claim 1, further comprising transferring the information stored in the database to a data reporting and analysis application, wherein the data reporting and analysis application generates one or more reports based on the information stored in the database.

12. The method of claim 1, wherein for at least a portion of the procedure records, the information sources from which the objective information about the medical imaging procedure and the subjective assessment of the result of the medical imaging procedure are collected are different.

13. The method of claim 1, wherein for at least a portion of the procedure records, the information sources from which the objective information about the medical imaging procedure and the subjective assessment of the result of the medical imaging procedure are collected are the same.

14. The method of claim 1, wherein the electronic report is structured to comprise a set of pre-defined attribute fields and the subjective assessment is entered into one of the pre-defined attribute fields.

15. The method of claim 1, further comprising:
forming a subject patient procedure record comprising the operating parameters of the suggested protocol and the subjective assessment of the result of the medical imaging procedure performed on the subject patient; and
storing the subject patient procedure record in the database.

16. A medical imaging system, comprising:
a plurality of medical imaging devices each comprising a user interface, wherein each of the medical imaging devices is configured to perform a medical imaging procedure on a subject patient according to a suggested protocol provided to the medical imaging device, wherein the suggested protocol comprises at least operating parameters of the medical imaging device;
one or more protocol management applications, wherein each of the protocol management applications is in electronic communication with one or more of the medical imaging devices; and
a database in electronic communication with each of the protocol management applications, wherein the database comprises a plurality of procedure records, wherein each of the procedure records comprises objective information about a past medical imaging procedure, including at least information about parameters used in the past medical imaging procedure and information about a patient that underwent the past medical imaging procedure, and a subjective assessment of a result of the past medical imaging procedure, wherein the subjective assessment of the result of the past medical imaging procedure comprises an individual's opinion of quality of the result of the past medical imaging procedure,
wherein the database is in electronic communication with a plurality of information sources configured to provide to the database objective information about medical imaging procedures and subjective assessments of results of the medical imaging procedures,
wherein the one or more protocol management applications are each configured to (a) receive demographic information about the subject patient, (b) access the database; (c) determine the suggested protocol based on a consideration of the demographic information of the subject patient and the objective information and the subjective assessments contained in the plurality of procedure records in the database, (d) deliver the suggested protocol to the medical imaging device so as to enable the medical imaging procedure to be performed thereby on the subject patient in accordance with the operating parameters of the suggested protocol or a modification thereof by an operator of the medical imaging device,
wherein each of the medical imaging devices is further configured to (a) present the suggested protocol of the medical imaging procedure to be performed on the subject patient using the medical imaging device on the user interface in a visually perceptible form, (b) permit a subjective assessment of a result of the medical imaging procedure performed on the subject patient using the medical imaging device to be entered into the user interface, and (c) generate an electronic report of the medical imaging procedure performed on the subject patient using the medical imaging device, wherein the subjective assessment of the result of the medical imaging procedure performed on the subject patient using the medical imaging device is entered into and stored as part of the electronic report.

17. The medical imaging system of claim 16, wherein the information sources include at least one medical record system.

18. A medical imaging system, comprising:
a medical imaging device comprising a user interface; and
a protocol management application in electronic communication with the medical imaging device;
wherein the medical imaging device is configured to perform a medical imaging procedure on a subject patient according to a suggested protocol provided by the protocol management application, wherein the suggested protocol comprises at least operating parameters of the medical imaging device;
wherein the protocol management application is in communication with a database, wherein the database comprises a plurality of procedure records, wherein each of the procedure records comprises objective information about a past medical imaging procedure, including at least information about parameters used in the past medical imaging procedure and information about a patient that underwent the past medical imaging procedure, and a subjective assessment of a result of the past medical imaging procedure, wherein the subjective assessment of the result of the past medical imaging procedure comprises an individual's opinion of quality of the result of the past medical imaging procedure,
wherein the database is in electronic communication with a plurality of information sources configured to provide to the database objective information about medical imaging procedures and subjective assessments of results of the medical imaging procedures,
wherein the protocol management application is configured to (a) receive demographic information about the subject patient, (b) access the database; (c) determine the suggested protocol based on a consideration of the demographic information of the subject patient and the objective information and the subjective assessments contained in the plurality of procedure records in the database, (d) deliver the suggested protocol to the medical imaging device so as to enable the medical imaging procedure to be performed thereby on the subject patient in accordance with the operating parameters of the suggested protocol or a modification thereof by an operator of the medical imaging device, and wherein the medical imaging device is further configured to (a) present the suggested protocol of the medical imaging procedure to be performed on the subject patient using the medical imaging device on the user interface in a visually perceptible form, (b) permit a subjective assessment of a result of the medical imaging procedure performed on the subject patient using the medical imaging device to be entered into the user interface, and (c) generate an electronic report of the medical imaging procedure performed on the subject patient using the medical imaging device, wherein the subjective assessment of the result of the medical imaging procedure performed on the subject patient using the medical imaging device is entered into and stored as part of the electronic report.

* * * * *

UNITED STATES PATENT AND TRADEMARK OFFICE
CERTIFICATE OF CORRECTION

PATENT NO. : 10,078,725 B2
APPLICATION NO. : 14/357224
DATED : September 18, 2018
INVENTOR(S) : Kalafut et al.

Page 1 of 1

Figure 5:
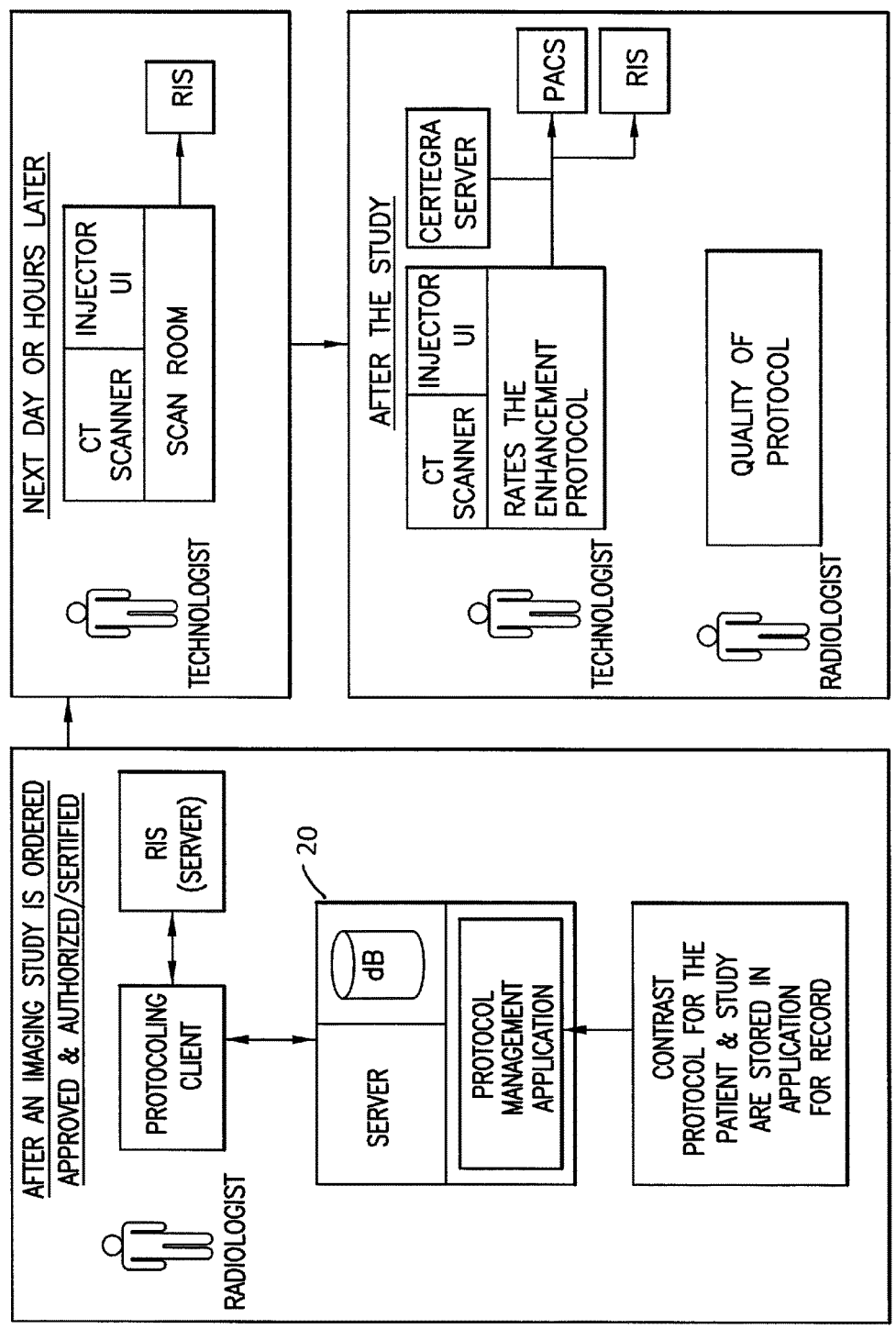
FIG. 5 illustrates a flowchart illustrating the distribution of information between different systems according to this disclosure.

It is certified that error appears in the above-identified patent and that said Letters Patent is hereby corrected as shown below:

In the Drawings
In Fig. 5, Sheet 5 of 23, delete "AUTHORIZED/SERTIFIED" and insert
-- AUTHORIZED/CERTIFIED --, therefor.
In Fig. 11, Sheet 11 of 23, under "HOSPITAL 1", Line 6, delete "STORSES" and insert
-- STORES --, therefor.

In the Specification
In Column 7, Line 4, delete "of FIG. 22." and insert -- of FIG. 20. --, therefor.
In Column 12, Line 41, delete "DICOM," and insert -- DICOM, HL7, --, therefor.
In Column 14, Line 52, delete ""( ):x/." and insert -- "( ):x/." --, therefor.
In Column 20, Line 35, delete "Angigophy," and insert -- Angiography, --, therefor.

Signed and Sealed this
Fourth Day of December, 2018

Andrei Iancu
*Director of the United States Patent and Trademark Office*